US012780937B2

(12) United States Patent
Mao et al.

(10) Patent No.: US 12,780,937 B2
(45) Date of Patent: Nov. 3, 2026

(54) ANTI-TROP-2 ANTIBODY, ANTIGEN-BINDING FRAGMENT THEREOF OR MUTANT THEREOF, AND MEDICAL USE THEREOF

(71) Applicants: Shanghai Hansoh Biomedical Co., Ltd., Shanghai (CN); Jiangsu Hansoh Pharmaceutical Group Co., Ltd., Lianyungang (CN)

(72) Inventors: Dongjie Mao, Shanghai (CN); Yan Luo, Shanghai (CN); Yuejun Xie, Shanghai (CN)

(73) Assignees: Shanghai Hansoh Biomedical Co., Ltd., Shanghai (CN); Jiangsu Hansoh Pharmaceutical Group Co., Ltd., Lianyungang (CN)

( * ) Notice: Subject to any disclaimer, the term of this patent is extended or adjusted under 35 U.S.C. 154(b) by 795 days.

(21) Appl. No.: 18/030,928

(22) PCT Filed: Oct. 14, 2021

(86) PCT No.: PCT/CN2021/123731

§ 371 (c)(1),
(2) Date: Apr. 7, 2023

(87) PCT Pub. No.: WO2022/078424

PCT Pub. Date: Apr. 21, 2022

(65) Prior Publication Data

US 2023/0374149 A1 Nov. 23, 2023

(30) Foreign Application Priority Data

Oct. 14, 2020 (CN) ......................... 202011099107.8

(51) Int. Cl.
*C07K 16/30* (2006.01)

(52) U.S. Cl.
CPC .......... *C07K 16/30* (2013.01); *C07K 2317/14* (2013.01); *C07K 2317/24* (2013.01); *C07K 2317/76* (2013.01); *C07K 2317/92* (2013.01)

(58) Field of Classification Search
CPC ................ C07K 16/30; C07K 2317/24; C07K 2317/565; G01N 33/575; A61P 35/00; A61K 2039/505
See application file for complete search history.

(56) References Cited

U.S. PATENT DOCUMENTS

| | | | |
|---|---|---|---|
| 5,840,854 A | 11/1998 | Hellstrom et al. | |
| 6,653,104 B2 | 11/2003 | Goldenberg | |
| 7,420,040 B2 | 9/2008 | Young et al. | |
| 10,501,555 B2 | 12/2019 | Guerra et al. | |
| 11,091,544 B2 | 8/2021 | Liu et al. | |
| 11,192,954 B2 | 12/2021 | Tang et al. | |
| 2016/0313339 A1 | 10/2016 | Goldenberg et al. | |
| 2021/0130496 A1* | 5/2021 | Chang | A61P 35/00 |

FOREIGN PATENT DOCUMENTS

| | | | |
|---|---|---|---|
| CN | 102827282 A | 12/2012 | |
| CN | 104053672 A | 9/2014 | |
| CN | 104114580 B | 7/2017 | |
| CN | 107406508 A | 11/2017 | |
| CN | 110317822 A | 10/2019 | |
| CN | 111018992 A | 4/2020 | |
| CN | 112243443 A | 1/2021 | |
| WO | 2015126548 A1 | 8/2015 | |
| WO | WO-2020191092 A1 * | 9/2020 | A61K 47/68031 |

OTHER PUBLICATIONS

Evans, "Vaccine therapy for cancer—fact or fiction?", 1999, Q. J. Med, 92, 299-307. (Year: 1999).*
Schiffman, "The Promise of Global Cervical-Cancer Prevention", 2005, The New England Journal of Medicine, 353(20), 2101-2104. (Year: 2005).*
Cuzick, "Overview of the main outcomes in breast-cancer prevention trials", 2003, The Lancet, 361, 296-300. (Year: 2003).*
Hernandez-Ledesma, "Lunasin, a novel seed peptide for cancer prevention", 2009, Peptides, 30, 426-430. (Year: 2009).*
Komenaka, "Immunotherapy for Melanoma", 2004, Clinics in Dermatology, 22, 251-265. (Year: 2004).*
International Search Report; China National Intellectual Property Administration; International Application No. PCT/CN2021/123731; Jan. 17, 2022; 10 pages.
Raji. R. et al. "Uterine and ovarian carcinosarcomas overexpressing Trop-2 are sensitive to hRS7. a humanized anti-Trop-2 antibody" Journal of Experimental and Cancer Research, vol. 30, No. 106, Nov. 10, 2011 (Nov. 10, 2011), pp. 1-7.
Written Opinion of the International Searching Authority; China National Intellectual Property Administration; International Application No. PCT/CN2021/123731; Jan. 17, 2022; 10 pages.
International Preliminary Report on Patentability; The International Bureau of WIPO; International Application No. PCT/CN2021/123731; Apr. 13, 2023; 11 pages.

* cited by examiner

*Primary Examiner* — Laura B Goddard
*Assistant Examiner* — Alyssa Rae Stonebraker
(74) *Attorney, Agent, or Firm* — Taft Stettinius & Hollister LLP

(57) ABSTRACT

The present invention relates to an anti-TROP-2 antibody, an antigen-binding fragment thereof or a mutant thereof, and a medical use thereof. Furthermore, the present application relates to a humanized anti-TROP-2 antibody mutant, a pharmaceutical composition comprising an anti-TROP-2 antibody mutant, a use thereof in the preparation of a drug for treating TROP-2-mediated diseases or conditions, and a use in tumor detection and diagnosis.

23 Claims, No Drawings

Specification includes a Sequence Listing.

SEQUENCE LISTING

```
<160> NUMBER OF SEQ ID NOS: 43

<210> SEQ ID NO 1
<211> LENGTH: 331
<212> TYPE: PRT
<213> ORGANISM: Homo sapiens

<400> SEQUENCE: 1

Met Ala Arg Gly Pro Gly Leu Ala Pro Pro Pro Leu Arg Leu Pro Leu
1               5                   10                  15

Leu Leu Leu Val Leu Ala Ala Val Thr Gly His Thr Ala Ala Gln Asp
            20                  25                  30

Asn Cys Thr Cys Pro Thr Asn Lys Met Thr Val Cys Ser Pro Asp Gly
        35                  40                  45

Pro Gly Gly Arg Cys Gln Cys Arg Ala Leu Gly Ser Gly Met Ala Val
    50                  55                  60
```

```
Asp Cys Ser Thr Leu Thr Ser Lys Cys Leu Leu Leu Lys Ala Arg Met
65                  70                  75                  80

Ser Ala Pro Lys Asn Ala Arg Thr Leu Val Arg Pro Ser Glu His Ala
                85                  90                  95

Leu Val Asp Asn Asp Gly Leu Tyr Asp Pro Asp Cys Asp Pro Glu Gly
            100                 105                 110

Arg Phe Lys Ala Arg Gln Cys Asn Gln Thr Ser Val Cys Trp Cys Val
        115                 120                 125

Asn Ser Val Gly Val Arg Arg Thr Asp Lys Gly Asp Leu Ser Leu Arg
    130                 135                 140

Cys Asp Glu Leu Val Arg Thr His His Ile Leu Ile Asp Leu Arg His
145                 150                 155                 160

Arg Pro Thr Ala Gly Ala Phe Asn His Ser Asp Leu Asp Ala Glu Leu
                165                 170                 175

Arg Arg Leu Phe Arg Glu Arg Tyr Arg Leu His Pro Lys Phe Val Ala
            180                 185                 190

Ala Val His Tyr Glu Gln Pro Thr Ile Gln Ile Glu Leu Arg Gln Asn
        195                 200                 205

Thr Ser Gln Lys Ala Ala Gly Asp Val Asp Ile Gly Asp Ala Ala Tyr
    210                 215                 220

Tyr Phe Glu Arg Asp Ile Lys Gly Glu Ser Leu Phe Gln Gly Arg Gly
225                 230                 235                 240

Gly Leu Asp Leu Arg Val Arg Gly Glu Pro Leu Gln Val Glu Arg Thr
                245                 250                 255

Leu Ile Tyr Tyr Leu Asp Glu Ile Pro Pro Lys Phe Ser Met Lys Arg
            260                 265                 270

Leu Thr Ala Gly Leu Ile Ala Val Ile Val Val Val Val Ala Leu
        275                 280                 285

Val Ala Gly Met Ala Val Leu Val Ile Thr Asn Arg Arg Lys Ser Gly
    290                 295                 300

Lys Tyr Lys Lys Val Glu Ile Lys Glu Leu Gly Glu Leu Arg Lys Glu
305                 310                 315                 320

Pro Ser Leu His His His His His His His His
                325                 330


<210> SEQ ID NO 2
<211> LENGTH: 121
<212> TYPE: PRT
<213> ORGANISM: Mus musculus

<400> SEQUENCE: 2

Gln Val Gln Leu Gln Gln Pro Gly Ala Glu Leu Val Arg Pro Gly Ala
1               5                   10                  15

Ser Val Lys Leu Ser Cys Arg Ala Ser Gly Tyr Thr Phe Thr Asn Tyr
            20                  25                  30

Trp Met Asn Trp Val Lys Gln Arg Pro Glu Gln Gly Leu Glu Trp Ile
        35                  40                  45

Gly Arg Ile Asp Pro Asn Asp Ser Glu Thr His Tyr Asn Gln Lys Phe
    50                  55                  60

Lys Asp Arg Ala Ile Leu Thr Val Asp Lys Ala Ser Asn Thr Ala Tyr
65                  70                  75                  80

Met Gln Leu Ser Gly Leu Thr Ser Glu Asp Ser Ala Val His Tyr Cys
                85                  90                  95

Ala Arg Ser Gly Phe Gly Ser Thr Tyr Trp Phe Phe Asp Val Trp Gly
```

100 105 110

Ala Gly Thr Thr Val Thr Val Ser Ser
115 120

<210> SEQ ID NO 3
<211> LENGTH: 107
<212> TYPE: PRT
<213> ORGANISM: Mus musculus

<400> SEQUENCE: 3

Asp Ile Val Met Thr Gln Ser His Lys Phe Met Ser Thr Ser Val Gly
1 5 10 15

Asp Arg Val Ser Ile Thr Cys Lys Ala Ser Gln Asp Val Ser Thr Ala
20 25 30

Val Ala Trp Tyr Gln Gln Lys Pro Gly Gln Ser Pro Lys Leu Leu Ile
35 40 45

Tyr Ser Ala Ser Tyr Arg Tyr Thr Gly Val Pro Asp Arg Phe Ala Gly
50 55 60

Ser Gly Tyr Gly Thr Asp Phe Thr Phe Thr Ile Ser Ser Val Gln Thr
65 70 75 80

Glu Asp Leu Thr Val Tyr His Cys Gln Gln His Tyr Ser Thr Pro Leu
85 90 95

Thr Phe Gly Pro Gly Thr Arg Leu Glu Leu Lys
100 105

<210> SEQ ID NO 4
<211> LENGTH: 5
<212> TYPE: PRT
<213> ORGANISM: Mus musculus

<400> SEQUENCE: 4

Asn Tyr Trp Met Asn
1 5

<210> SEQ ID NO 5
<211> LENGTH: 17
<212> TYPE: PRT
<213> ORGANISM: Mus musculus

<400> SEQUENCE: 5

Arg Ile Asp Pro Asn Asp Ser Glu Thr His Tyr Asn Gln Lys Phe Lys
1 5 10 15

Asp

<210> SEQ ID NO 6
<211> LENGTH: 12
<212> TYPE: PRT
<213> ORGANISM: Mus musculus

<400> SEQUENCE: 6

Ser Gly Phe Gly Ser Thr Tyr Trp Phe Phe Asp Val
1 5 10

<210> SEQ ID NO 7
<211> LENGTH: 11
<212> TYPE: PRT
<213> ORGANISM: Mus musculus

<400> SEQUENCE: 7

Lys Ala Ser Gln Asp Val Ser Thr Ala Val Ala
1 5 10

<210> SEQ ID NO 8
<211> LENGTH: 7
<212> TYPE: PRT
<213> ORGANISM: Mus musculus

<400> SEQUENCE: 8

```
Ser Ala Ser Tyr Arg Tyr Thr
1               5
```

<210> SEQ ID NO 9
<211> LENGTH: 9
<212> TYPE: PRT
<213> ORGANISM: Mus musculus

<400> SEQUENCE: 9

```
Gln Gln His Tyr Ser Thr Pro Leu Thr
1               5
```

<210> SEQ ID NO 10
<211> LENGTH: 121
<212> TYPE: PRT
<213> ORGANISM: Artificial Sequence
<220> FEATURE:
<221> NAME/KEY: DOMAIN
<222> LOCATION:
<223> OTHER INFORMATION: Variable region

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Asn Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser
        115                 120
```

<210> SEQ ID NO 11
<211> LENGTH: 107
<212> TYPE: PRT
<213> ORGANISM: Artificial Sequence
<220> FEATURE:
<221> NAME/KEY: DOMAIN
<222> LOCATION:
<223> OTHER INFORMATION: Variable region

<400> SEQUENCE: 11

```
Asp Val Val Met Thr Gln Ser Pro Leu Ser Leu Pro Val Thr Leu Gly
1               5                   10                  15

Gln Pro Ala Ser Ile Ser Cys Lys Ala Ser Gln Asp Val Ser Thr Ala
            20                  25                  30

Val Ala Trp Tyr Gln Gln Lys Pro Gly Lys Ala Pro Lys Leu Phe Ile
        35                  40                  45
```

```
Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Leu
                85                  90                  95

Thr Phe Gly Gln Gly Thr Arg Leu Glu Ile Lys
            100                 105


<210> SEQ ID NO 12
<211> LENGTH: 330
<212> TYPE: PRT
<213> ORGANISM: Homo sapiens

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

```
305                 310                 315                 320

Gln Lys Ser Leu Ser Leu Ser Pro Gly Lys
                325                 330


<210> SEQ ID NO 13
<211> LENGTH: 107
<212> TYPE: PRT
<213> ORGANISM: Homo sapiens

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 14
<211> LENGTH: 451
<212> TYPE: PRT
<213> ORGANISM: Artificial Sequence
<220> FEATURE:
<221> NAME/KEY: CHAIN
<222> LOCATION:
<223> OTHER INFORMATION: Heavy chain

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Asn Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 15
<211> LENGTH: 214
<212> TYPE: PRT
<213> ORGANISM: Artificial Sequence
<220> FEATURE:
<221> NAME/KEY: CHAIN
<222> LOCATION:
<223> OTHER INFORMATION: Light chain

<400> SEQUENCE: 15

Asp Val Val Met Thr Gln Ser Pro Leu Ser Leu Pro Val Thr Leu Gly
1               5                   10                  15

Gln Pro Ala Ser Ile Ser Cys Lys Ala Ser Gln Asp Val Ser Thr Ala
            20                  25                  30

Val Ala Trp Tyr Gln Gln Lys Pro Gly Lys Ala Pro Lys Leu Phe Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln His Tyr Ser Thr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 16
<211> LENGTH: 121
<212> TYPE: PRT
<213> ORGANISM: Artificial Sequence
<220> FEATURE:
<221> NAME/KEY: DOMAIN
<222> LOCATION:
<223> OTHER INFORMATION: Variable region

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Arg Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser
        115                 120


<210> SEQ ID NO 17
<211> LENGTH: 121
<212> TYPE: PRT
<213> ORGANISM: Artificial Sequence
<220> FEATURE:
<221> NAME/KEY: DOMAIN
<222> LOCATION:
<223> OTHER INFORMATION: Variable region

<400> SEQUENCE: 17

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Tyr Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser
        115                 120

<210> SEQ ID NO 18
<211> LENGTH: 121
<212> TYPE: PRT
<213> ORGANISM: Artificial Sequence
<220> FEATURE:
<221> NAME/KEY: DOMAIN
<222> LOCATION:
<223> OTHER INFORMATION: Variable region

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Gln Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser
        115                 120

<210> SEQ ID NO 19
<211> LENGTH: 121
<212> TYPE: PRT
<213> ORGANISM: Artificial Sequence
<220> FEATURE:
<221> NAME/KEY: DOMAIN
<222> LOCATION:
<223> OTHER INFORMATION: Variable region

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

```
Gly Arg Ile Asp Pro Leu Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser
        115                 120


<210> SEQ ID NO 20
<211> LENGTH: 121
<212> TYPE: PRT
<213> ORGANISM: Artificial Sequence
<220> FEATURE:
<221> NAME/KEY: DOMAIN
<222> LOCATION:
<223> OTHER INFORMATION: Variable region

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Thr Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser
        115                 120


<210> SEQ ID NO 21
<211> LENGTH: 451
<212> TYPE: PRT
<213> ORGANISM: Artificial Sequence
<220> FEATURE:
<221> NAME/KEY: CHAIN
<222> LOCATION:
<223> OTHER INFORMATION: Heavy chain

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Arg Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
```

-continued

```
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 22
<211> LENGTH: 451
<212> TYPE: PRT
<213> ORGANISM: Artificial Sequence
<220> FEATURE:
<221> NAME/KEY: CHAIN
<222> LOCATION:
```

<223> OTHER INFORMATION: Heavy chain

<400> SEQUENCE: 22

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Tyr Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 23
<211> LENGTH: 451
<212> TYPE: PRT
<213> ORGANISM: Artificial Sequence
<220> FEATURE:
<221> NAME/KEY: CHAIN
<222> LOCATION:
<223> OTHER INFORMATION: Heavy chain

<400> SEQUENCE: 23

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Val Ser Asn Tyr
20 25 30

Trp Met Asn Trp Val Arg Gln Ala Pro Gly Lys Gly Leu Glu Trp Met
35 40 45

Gly Arg Ile Asp Pro Gln Asp Ser Glu Thr His Tyr Asn Gln Lys Phe
50 55 60

Lys Asp Arg Val Thr Ile Ser Val Asp Lys Ser Lys Asn Gln Phe Ser
65 70 75 80

Leu Lys Leu Ser Ser Val Thr Ala Ala Asp Thr Ala Val Tyr Tyr Cys
85 90 95

Ala Arg Ser Gly Phe Gly Ser Thr Tyr Trp Phe Phe Asp Val Trp Gly
100 105 110

Gln Gly Thr Thr Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr

```
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 24
<211> LENGTH: 451
<212> TYPE: PRT
<213> ORGANISM: Artificial Sequence
<220> FEATURE:
<221> NAME/KEY: CHAIN
<222> LOCATION:
<223> OTHER INFORMATION: Heavy chain

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Leu Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 25
<211> LENGTH: 451
<212> TYPE: PRT
<213> ORGANISM: Artificial Sequence
<220> FEATURE:
<221> NAME/KEY: CHAIN
<222> LOCATION:
<223> OTHER INFORMATION: Heavy chain

<400> SEQUENCE: 25

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Thr Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80
```

```
Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 26
<211> LENGTH: 17
<212> TYPE: PRT
<213> ORGANISM: Artificial Sequence
<220> FEATURE:
<221> NAME/KEY: DOMAIN

<222> LOCATION:
<223> OTHER INFORMATION: CDR

<400> SEQUENCE: 26

Arg Ile Asp Pro Arg Asp Ser Glu Thr His Tyr Asn Gln Lys Phe Lys
1 5 10 15

Asp

<210> SEQ ID NO 27
<211> LENGTH: 17
<212> TYPE: PRT
<213> ORGANISM: Artificial Sequence
<220> FEATURE:
<221> NAME/KEY: DOMAIN
<222> LOCATION:
<223> OTHER INFORMATION: CDR

<400> SEQUENCE: 27

Arg Ile Asp Pro Tyr Asp Ser Glu Thr His Tyr Asn Gln Lys Phe Lys
1 5 10 15

Asp

<210> SEQ ID NO 28
<211> LENGTH: 17
<212> TYPE: PRT
<213> ORGANISM: Artificial Sequence
<220> FEATURE:
<221> NAME/KEY: DOMAIN
<222> LOCATION:
<223> OTHER INFORMATION: CDR

<400> SEQUENCE: 28

Arg Ile Asp Pro Gln Asp Ser Glu Thr His Tyr Asn Gln Lys Phe Lys
1 5 10 15

Asp

<210> SEQ ID NO 29
<211> LENGTH: 17
<212> TYPE: PRT
<213> ORGANISM: Artificial Sequence
<220> FEATURE:
<221> NAME/KEY: DOMAIN
<222> LOCATION:
<223> OTHER INFORMATION: CDR

<400> SEQUENCE: 29

Arg Ile Asp Pro Leu Asp Ser Glu Thr His Tyr Asn Gln Lys Phe Lys
1 5 10 15

Asp

<210> SEQ ID NO 30
<211> LENGTH: 17
<212> TYPE: PRT
<213> ORGANISM: Artificial Sequence
<220> FEATURE:
<221> NAME/KEY: DOMAIN
<222> LOCATION:
<223> OTHER INFORMATION: CDR

<400> SEQUENCE: 30

Arg Ile Asp Pro Thr Asp Ser Glu Thr His Tyr Asn Gln Lys Phe Lys
1 5 10 15

Asp

<210> SEQ ID NO 31
<211> LENGTH: 121
<212> TYPE: PRT
<213> ORGANISM: Artificial Sequence
<220> FEATURE:
<221> NAME/KEY: DOMAIN
<222> LOCATION:
<223> OTHER INFORMATION: Variable region

<400> SEQUENCE: 31

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Ile Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser
        115                 120
```

<210> SEQ ID NO 32
<211> LENGTH: 121
<212> TYPE: PRT
<213> ORGANISM: Artificial Sequence
<220> FEATURE:
<221> NAME/KEY: DOMAIN
<222> LOCATION:
<223> OTHER INFORMATION: Variable region

<400> SEQUENCE: 32

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Phe Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser
        115                 120
```

<210> SEQ ID NO 33
<211> LENGTH: 121
<212> TYPE: PRT
<213> ORGANISM: Artificial Sequence
<220> FEATURE:
<221> NAME/KEY: DOMAIN
<222> LOCATION:

<223> OTHER INFORMATION: Variable region

<400> SEQUENCE: 33

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Val Ser Asn Tyr
20 25 30

Trp Met Asn Trp Val Arg Gln Ala Pro Gly Lys Gly Leu Glu Trp Met
35 40 45

Gly Arg Ile Asp Pro Glu Asp Ser Glu Thr His Tyr Asn Gln Lys Phe
50 55 60

Lys Asp Arg Val Thr Ile Ser Val Asp Lys Ser Lys Asn Gln Phe Ser
65 70 75 80

Leu Lys Leu Ser Ser Val Thr Ala Ala Asp Thr Ala Val Tyr Tyr Cys
85 90 95

Ala Arg Ser Gly Phe Gly Ser Thr Tyr Trp Phe Phe Asp Val Trp Gly
100 105 110

Gln Gly Thr Thr Val Thr Val Ser Ser
115 120

<210> SEQ ID NO 34
<211> LENGTH: 121
<212> TYPE: PRT
<213> ORGANISM: Artificial Sequence
<220> FEATURE:
<221> NAME/KEY: DOMAIN
<222> LOCATION:
<223> OTHER INFORMATION: Variable region

<400> SEQUENCE: 34

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Val Ser Asn Tyr
20 25 30

Trp Met Asn Trp Val Arg Gln Ala Pro Gly Lys Gly Leu Glu Trp Met
35 40 45

Gly Arg Ile Asp Pro Ala Asp Ser Glu Thr His Tyr Asn Gln Lys Phe
50 55 60

Lys Asp Arg Val Thr Ile Ser Val Asp Lys Ser Lys Asn Gln Phe Ser
65 70 75 80

Leu Lys Leu Ser Ser Val Thr Ala Ala Asp Thr Ala Val Tyr Tyr Cys
85 90 95

Ala Arg Ser Gly Phe Gly Ser Thr Tyr Trp Phe Phe Asp Val Trp Gly
100 105 110

Gln Gly Thr Thr Val Thr Val Ser Ser
115 120

<210> SEQ ID NO 35
<211> LENGTH: 451
<212> TYPE: PRT
<213> ORGANISM: Artificial Sequence
<220> FEATURE:
<221> NAME/KEY: CHAIN
<222> LOCATION:
<223> OTHER INFORMATION: Heavy chain

<400> SEQUENCE: 35

Glu Val Gln Leu Leu Glu Ser Gly Gly Gly Leu Val Gln Pro Gly Gly
1 5 10 15

-continued

```
Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Ile Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
```

```
        435                 440                 445

Pro Gly Lys
    450


<210> SEQ ID NO 36
<211> LENGTH: 451
<212> TYPE: PRT
<213> ORGANISM: Artificial Sequence
<220> FEATURE:
<221> NAME/KEY: CHAIN
<222> LOCATION:
<223> OTHER INFORMATION: Heavy chain

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Phe Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

Glu Lys Thr Ile Ser Lys Ala Lys Gly Gln Pro Arg Glu Pro Gln Val
340 345 350

Tyr Thr Leu Pro Pro Ser Arg Asp Glu Leu Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 37
<211> LENGTH: 451
<212> TYPE: PRT
<213> ORGANISM: Artificial Sequence
<220> FEATURE:
<221> NAME/KEY: CHAIN
<222> LOCATION:
<223> OTHER INFORMATION: Heavy chain

<400> SEQUENCE: 37

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Val Ser Asn Tyr
20 25 30

Trp Met Asn Trp Val Arg Gln Ala Pro Gly Lys Gly Leu Glu Trp Met
35 40 45

Gly Arg Ile Asp Pro Glu Asp Ser Glu Thr His Tyr Asn Gln Lys Phe
50 55 60

Lys Asp Arg Val Thr Ile Ser Val Asp Lys Ser Lys Asn Gln Phe Ser
65 70 75 80

Leu Lys Leu Ser Ser Val Thr Ala Ala Asp Thr Ala Val Tyr Tyr Cys
85 90 95

Ala Arg Ser Gly Phe Gly Ser Thr Tyr Trp Phe Phe Asp Val Trp Gly
100 105 110

Gln Gly Thr Thr Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 38
<211> LENGTH: 451
<212> TYPE: PRT
<213> ORGANISM: Artificial Sequence
<220> FEATURE:
<221> NAME/KEY: CHAIN
<222> LOCATION:
<223> OTHER INFORMATION: Heavy chain

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Trp Met Asn Trp Val Arg Gln Ala Pro Gly Lys Gly Leu Glu Trp Met
        35                  40                  45

Gly Arg Ile Asp Pro Ala Asp Ser Glu Thr His Tyr Asn Gln Lys Phe
    50                  55                  60

Lys Asp Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Phe Gly Ser Thr Tyr Trp Phe Phe Asp Val Trp Gly
            100                 105                 110

Gln Gly Thr Thr Val Thr Val Ser Ser Ala Ser Thr Lys Gly Pro Ser
```

```
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 39
<211> LENGTH: 17
<212> TYPE: PRT
<213> ORGANISM: Artificial Sequence
<220> FEATURE:
<221> NAME/KEY: DOMAIN
<222> LOCATION:
<223> OTHER INFORMATION: CDR

<400> SEQUENCE: 39

Arg Ile Asp Pro Ile Asp Ser Glu Thr His Tyr Asn Gln Lys Phe Lys
1               5                   10                  15
```

Asp

<210> SEQ ID NO 40
<211> LENGTH: 17
<212> TYPE: PRT
<213> ORGANISM: Artificial Sequence
<220> FEATURE:
<221> NAME/KEY: DOMAIN
<222> LOCATION:
<223> OTHER INFORMATION: CDR

<400> SEQUENCE: 40

Arg Ile Asp Pro Phe Asp Ser Glu Thr His Tyr Asn Gln Lys Phe Lys
1 5 10 15

Asp

<210> SEQ ID NO 41
<211> LENGTH: 17
<212> TYPE: PRT
<213> ORGANISM: Artificial Sequence
<220> FEATURE:
<221> NAME/KEY: DOMAIN
<222> LOCATION:
<223> OTHER INFORMATION: CDR

<400> SEQUENCE: 41

Arg Ile Asp Pro Glu Asp Ser Glu Thr His Tyr Asn Gln Lys Phe Lys
1 5 10 15

Asp

<210> SEQ ID NO 42
<211> LENGTH: 17
<212> TYPE: PRT
<213> ORGANISM: Artificial Sequence
<220> FEATURE:
<221> NAME/KEY: DOMAIN
<222> LOCATION:
<223> OTHER INFORMATION: CDR

<400> SEQUENCE: 42

Arg Ile Asp Pro Ala Asp Ser Glu Thr His Tyr Asn Gln Lys Phe Lys
1 5 10 15

Asp

<210> SEQ ID NO 43
<211> LENGTH: 17
<212> TYPE: PRT
<213> ORGANISM: Artificial Sequence
<220> FEATURE:
<221> NAME/KEY: VARIANT
<222> LOCATION: (5)..(5)
<223> OTHER INFORMATION: X is selected from the group consisting of R, Y, Q, L, T, I, F, E and A
<220> FEATURE:
<221> NAME/KEY: DOMAIN
<222> LOCATION:
<223> OTHER INFORMATION: CDR

<400> SEQUENCE: 43

Arg Ile Asp Pro Xaa Asp Ser Glu Thr His Tyr Asn Gln Lys Phe Lys
1 5 10 15

Asp

ANTI-TROP-2 ANTIBODY, ANTIGEN-BINDING FRAGMENT THEREOF OR MUTANT THEREOF, AND MEDICAL USE THEREOF

CROSS-REFERENCE TO RELATED APPLICATIONS

The present application is a U.S. National Stage application of International Application No. PCT/CN2021/123731 filed on Oct. 14, 2021, which claims the priority of the Chinese Patent Application No. 202011099107.8 filed on Oct. 14, 2020. The contents of each of those applications are incorporated herein by reference in their entireties.

FIELD OF THE INVENTION

The present disclosure relates to an anti-TROP-2 antibody, an antigen-binding fragment thereof or a mutant thereof, relates to a chimeric antibody or a humanized antibody comprising the CDR region of the anti-TROP-2 antibody or a mutant thereof, and relates to a pharmaceutical composition comprising human anti-TROP-2 antibody, an antigen-binding fragment thereof or a mutant thereof, as well as relates to the use thereof as an anti-cancer drug and a use thereof for the detection or diagnosis of tumors.

BACKGROUND OF THE INVENTION

With the deepening of the study of tumor genomics, proteomics and signaling pathways, the interaction of oncogenes and tumor suppressor genes in tumor cells and their impact on the tumor microenvironment have become clearer, which also makes it possible to design new antitumor therapeutic schemes for specific molecular targets of tumors.

Molecular targeted treatment for tumors is a new treatment mode different from traditional surgery, radiotherapy and chemotherapy, and the advantage is that the drug usually only binds to the corresponding target, and kills or inhibits the target cell by directly affecting the function of the target molecule or by the physical or chemical effector molecule it carries. Due to the specific target, the drug is usually highly selective, and can effectively kill or inhibit the target cell while producing no or only little toxic side effect on normal tissue cells. Therefore, the development of molecular targeted drugs has become a hot spot in tumor clinical research.

Trophoblast cell surface antigen 2 (TROP-2), also known as tumor-associated calcium signal transducer 2 (TACSTD2), is a cellular transmembrane glycoprotein encoded by the TACSTD2 gene. TROP-2 consists of about 323 amino acids, of which the signal peptide comprises 26 amino acids, the extracellular region comprises 248 amino acids, the transmembrane region comprises 23 amino acids, and the cytosolic region comprises 26 amino acids. There are 4 heterogeneous N-linked glycosylation sites in the extracellular domain of TROP-2, and the apparent molecular weight increases by 11 to 13 KD after adding sugar chains. In the TACSTD gene family, the extracellular domain has a characteristic thyroglobulin (TY) sequence, which is usually thought to be associated with the proliferation, infiltration and metastasis of cancer cells.

To date, no physiologic ligand of TROP-2 has been identified, and the molecular function of TROP-2 has not been elucidated. However, due to the phosphorylation at the intracellular Serine 303 residue by protein kinase C (PKC, which belongs to $Ca^{2+}$-dependent protein kinases) and the presence of PIP2-binding sequence in the intracellular domain, TROP-2 is demonstrated to have signaling functions in tumor cells.

A large number of clinical studies and literature reports have shown that TROP-2 antigen is overexpressed in a variety of epithelial-derived cancers, such as gastric cancer, lung cancer, colorectal cancer, ovarian cancer, breast cancer, prostate cancer, pancreatic cancer, liver cancer, esophageal cancer and the like. The TROP-2 antigen is rarely expressed or not expressed in normal tissues in adults, only rarely expressed in cells in the epithelial region, and the expression level is also lower than that in cancer cells, indicating that TROP-2 is associated with tumor formation. Overexpression of TROP-2 in tumor tissues is closely related to poor prognosis and metastasis of cancer cells, while affecting the overall survival of subjects. As a result, TROP-2 has become a compelling target in molecular targeted treatments for tumors.

Currently, studies have reported the anti-tumor effects of a variety of TROP-2 antibodies:

U.S. Pat. No. 5,840,854 reports the cytotoxicity of a cytotoxin-conjugated anti-TROP-2 monoclonal antibody (BR110) against human cancer cell lines H3619, H2987, MCF-7, H3396 and H2981.

U.S. Pat. No. 6,653,104 discloses an antibody (RS7), which was labeled with radioactive substances and tested in an in vivo model, and showed antitumor activity in a nude mice xenograft model, but no antitumor effect of the naked antibody was reported.

In addition, U.S. Pat. No. 7,420,040 reports that isolated monoclonal antibodies, generated by hybridoma cell lines AR47A6.4.2 or AR52A301.5 obtained by immunizing mice with human ovarian cancer tissue, bind to TROP-2 antigens and display antitumor activity in a nude mice xenograft model.

CN102827282A discloses a genetically engineered human anti-TROP-2 antibody IgG and the use thereof. The results of in vitro tests showed that this anti-TROP-2 antibody IgG had a significant inhibitory effect on the proliferation of pancreatic cancer cells.

CN104114580A discloses an antibody (especially a humanized antibody) that specifically reacts with TROP-2 antigen and has antitumor activity in vivo, as well as a hybridoma that produces the antibody, a complex of the antibody and an agent, a pharmaceutical composition for the diagnosis or treatment of tumors, a detection method for tumors, and a kit for the detection or diagnosis of tumors.

However, it is challenging to find monoclonal antibodies with high affinity, high specificity, and potent cytotoxicity or tumor-killing/inhibitory/degenerative activity. Therefore, there is still an urgent need to develop TROP-2 antibodies and other immunotherapeutic agents with good efficacy, high safety and suitable for human subjects.

SUMMARY OF THE INVENTION

The present disclosure provides an anti-TROP-2 antibody, an antigen-binding fragment thereof or a mutant thereof, which comprises a heavy chain variable region and a light chain variable region.

In a preferred embodiment of the anti-TROP-2 antibody, antigen-binding fragment thereof or mutant thereof of the present disclosure, wherein:

the heavy chain variable region comprises at least one HCDR as shown in the sequence selected from the group consisting of:

SEQ ID NO: 4, SEQ ID NO: 43 and SEQ ID NO: 6; and the light chain variable region comprises at least one LCDR as shown in the sequence selected from the group consisting of:

SEQ ID NO: 7, SEQ ID NO: 8 and SEQ ID NO: 9;

wherein, SEQ ID NO: 43 is as shown in RIDPXDS-ETHYNQKFKD, the X is selected from the group consisting of amino acid residues R, Y, Q, L, T, I, F, E and A.

In a preferred embodiment of the present disclosure, the heavy chain variable region HCDR2 is selected from the group consisting of SEQ ID NO: 26, SEQ ID NO: 27, SEQ ID NO: 28, SEQ ID NO: 29, SEQ ID NO: 30, SEQ ID NO: 39, SEQ ID NO: 40, SEQ ID NO: 41 and SEQ ID NO: 42.

In a preferred embodiment of the anti-TROP-2 antibody, antigen-binding fragment thereof or mutant thereof of the present disclosure, the antibody heavy chain variable region comprises:

HCDR1 as shown in SEQ ID NO: 4, HCDR2 as shown in SEQ ID NO: 26 and HCDR3 as shown in SEQ ID NO: 6; or HCDR1 as shown in SEQ ID NO: 4, HCDR2 as shown in SEQ ID NO: 27 and HCDR3 as shown in SEQ ID NO: 6; or HCDR1 as shown in SEQ ID NO: 4, HCDR2 as shown in SEQ ID NO: 28 and HCDR3 as shown in SEQ ID NO: 6; or HCDR1 as shown in SEQ ID NO: 4, HCDR2 as shown in SEQ ID NO: 29 and HCDR3 as shown in SEQ ID NO: 6; or HCDR1 as shown in SEQ ID NO: 4, HCDR2 as shown in SEQ ID NO: 30 and HCDR3 as shown in SEQ ID NO: 6; or HCDR1 as shown in SEQ ID NO: 4, HCDR2 as shown in SEQ ID NO: 39 and HCDR3 as shown in SEQ ID NO: 6; or HCDR1 as shown in SEQ ID NO: 4, HCDR2 as shown in SEQ ID NO: 40 and HCDR3 as shown in SEQ ID NO: 6; or HCDR1 as shown in SEQ ID NO: 4, HCDR2 as shown in SEQ ID NO: 41 and HCDR3 as shown in SEQ ID NO: 6; or HCDR1 as shown in SEQ ID NO: 4, HCDR2 as shown in SEQ ID NO: 42 and HCDR3 as shown in SEQ ID NO: 6.

In a preferred embodiment of the anti-TROP-2 antibody, antigen-binding fragment thereof or mutant thereof of the present disclosure, the light chain variable region comprises:

LCDR1 as shown in SEQ ID NO: 7, LCDR2 as shown in SEQ ID NO: 8 and LCDR3 as shown in SEQ ID NO: 9.

In a preferred embodiment of the anti-TROP-2 antibody, antigen-binding fragment thereof or mutant thereof of the present disclosure, wherein:

the heavy chain variable region comprises: HCDR1 as shown in SEQ ID NO: 4, HCDR2 as shown in SEQ ID NO: 26 and HCDR3 as shown in SEQ ID NO: 6; and the light chain variable region comprises: LCDR1 as shown in SEQ ID NO: 7, LCDR2 as shown in SEQ ID NO: 8 and LCDR3 as shown in SEQ ID NO: 9.

In a preferred embodiment of the anti-TROP-2 antibody, antigen-binding fragment thereof or mutant thereof of the present disclosure, wherein:

the heavy chain variable region comprises: HCDR1 as shown in SEQ ID NO: 4, HCDR2 as shown in SEQ ID NO: 27 and HCDR3 as shown in SEQ ID NO: 6; and the light chain variable region comprises: LCDR1 as shown in SEQ ID NO: 7, LCDR2 as shown in SEQ ID NO: 8 and LCDR3 as shown in SEQ ID NO: 9.

In a preferred embodiment of the anti-TROP-2 antibody, antigen-binding fragment thereof or mutant thereof of the present disclosure, wherein:

the heavy chain variable region comprises: HCDR1 as shown in SEQ ID NO: 4, HCDR2 as shown in SEQ ID NO: 28 and HCDR3 as shown in SEQ ID NO: 6; and the light chain variable region comprises: LCDR1 as shown in SEQ ID NO: 7, LCDR2 as shown in SEQ ID NO: 8 and LCDR3 as shown in SEQ ID NO: 9.

In a preferred embodiment of the anti-TROP-2 antibody, antigen-binding fragment thereof or mutant thereof of the present disclosure, wherein:

the heavy chain variable region comprises: HCDR1 as shown in SEQ ID NO: 4, HCDR2 as shown in SEQ ID NO: 29 and HCDR3 as shown in SEQ ID NO: 6; and the light chain variable region comprises: LCDR1 as shown in SEQ ID NO: 7, LCDR2 as shown in SEQ ID NO: 8 and LCDR3 as shown in SEQ ID NO: 9.

In a preferred embodiment of the anti-TROP-2 antibody, antigen-binding fragment thereof or mutant thereof of the present disclosure, wherein:

the heavy chain variable region comprises: HCDR1 as shown in SEQ ID NO: 4, HCDR2 as shown in SEQ ID NO: 30 and HCDR3 as shown in SEQ ID NO: 6; and the light chain variable region comprises: LCDR1 as shown in SEQ ID NO: 7, LCDR2 as shown in SEQ ID NO: 8 and LCDR3 as shown in SEQ ID NO: 9.

In a preferred embodiment of the anti-TROP-2 antibody, antigen-binding fragment thereof or mutant thereof of the present disclosure, wherein:

the heavy chain variable region comprises: HCDR1 as shown in SEQ ID NO: 4, HCDR2 as shown in SEQ ID NO: 39 and HCDR3 as shown in SEQ ID NO: 6; and the light chain variable region comprises: LCDR1 as shown in SEQ ID NO: 7, LCDR2 as shown in SEQ ID NO: 8 and LCDR3 as shown in SEQ ID NO: 9.

In a preferred embodiment of the anti-TROP-2 antibody, antigen-binding fragment thereof or mutant thereof of the present disclosure, wherein:

the heavy chain variable region comprises: HCDR1 as shown in SEQ ID NO: 4, HCDR2 as shown in SEQ ID NO: 40 and HCDR3 as shown in SEQ ID NO: 6; and the light chain variable region comprises: LCDR1 as shown in SEQ ID NO: 7, LCDR2 as shown in SEQ ID NO: 8 and LCDR3 as shown in SEQ ID NO: 9.

In a preferred embodiment of the anti-TROP-2 antibody, antigen-binding fragment thereof or mutant thereof of the present disclosure, wherein:

the heavy chain variable region comprises: HCDR1 as shown in SEQ ID NO: 4, HCDR2 as shown in SEQ ID NO: 41 and HCDR3 as shown in SEQ ID NO: 6; and the light chain variable region comprises: LCDR1 as shown in SEQ ID NO: 7, LCDR2 as shown in SEQ ID NO: 8 and LCDR3 as shown in SEQ ID NO: 9.

In a preferred embodiment of the anti-TROP-2 antibody, antigen-binding fragment thereof or mutant thereof of the present disclosure, wherein:

the heavy chain variable region comprises: HCDR1 as shown in SEQ ID NO: 4, HCDR2 as shown in SEQ ID NO: 42 and HCDR3 as shown in SEQ ID NO: 6; and the light chain variable region comprises: LCDR1 as shown in SEQ ID NO: 7, LCDR2 as shown in SEQ ID NO: 8 and LCDR3 as shown in SEQ ID NO: 9.

In a preferred embodiment of the anti-TROP-2 antibody, antigen-binding fragment thereof or mutant thereof of the present disclosure, the antibody is a murine antibody, a chimeric antibody, a human antibody or a humanized antibody.

In a preferred embodiment of the anti-TROP-2 antibody, antigen-binding fragment thereof or mutant thereof of the present disclosure, the anti-TROP-2 antibody or antigen-binding fragment thereof further comprises a constant region derived from human IgG1, IgG2, IgG3 or IgG4 or a mutant thereof.

In a further preferred embodiment of the present disclosure, the anti-TROP-2 antibody, antigen-binding fragment thereof or mutant thereof further comprises a heavy chain constant region derived from human IgG1, IgG2 or IgG4 or a mutant thereof.

In a further preferred embodiment of the present disclosure, the anti-TROP-2 antibody, antigen-binding fragment thereof or mutant thereof further comprises a heavy chain constant region derived from IgG1 with enhanced ADCC toxicity after amino acid mutation.

In a further preferred embodiment of the present disclosure, the anti-TROP-2 antibody, antigen-binding fragment thereof or mutant thereof further comprises a heavy chain constant region of IgG1 introduced with 239D and 241L mutations.

In a further preferred embodiment of the present disclosure, the anti-TROP-2 antibody, antigen-binding fragment thereof or mutant thereof further comprises a heavy chain constant region selected from SEQ ID NO: 12.

In a further preferred embodiment of the present disclosure, the anti-TROP-2 antibody, antigen-binding fragment thereof or mutant thereof further comprises a light chain constant region derived from human κ chain, λ chain or a mutant thereof.

In a further preferred embodiment of the present disclosure, the anti-TROP-2 antibody, antigen-binding fragment thereof or mutant thereof further comprises a light chain constant region selected from SEQ ID NO: 13.

In a preferred embodiment of the anti-TROP-2 antibody, antigen-binding fragment thereof or mutant thereof of the present disclosure, the anti-TROP-2 antibody, antigen-binding fragment thereof or mutant thereof comprises a heavy chain variable region selected from the group consisting of SEQ ID NO: 16, SEQ ID NO: 17, SEQ ID NO: 18, SEQ ID NO: 19, SEQ ID NO: 20, SEQ ID NO: 31, SEQ ID NO: 32, SEQ ID NO: 33, SEQ ID NO: 34, or a heavy chain variable region having at least 70%, 75%, 80%, 85%, 90%, 95% or 99% identity with the same.

In a preferred embodiment of the anti-TROP-2 antibody, antigen-binding fragment thereof or mutant thereof of the present disclosure, the anti-TROP-2 antibody, antigen-binding fragment thereof or mutant thereof comprises the light chain variable region of SEQ ID NO: 11, or a light chain variable region having at least 70%, 75%, 80%, 85%, 90%, 95% or 99% identity with the same.

In a preferred embodiment of the present disclosure, the anti-TROP-2 antibody or mutant thereof comprises a heavy chain selected from the group consisting of SEQ ID NO: 21, SEQ ID NO: 22, SEQ ID NO: 23, SEQ ID NO: 24, SEQ ID NO: 25, SEQ ID NO: 35, SEQ ID NO: 36, SEQ ID NO: 37, SEQ ID NO: 38, or a full-length heavy chain having at least 80%, 85%, 90%, 95% or 99% identity with the same.

In a preferred embodiment of the present disclosure, the anti-TROP-2 antibody or mutant thereof comprises the light chain of SEQ ID NO: 15, or a full-length light chain having at least 80%, 85%, 90%, 95% or 99% identity with the same.

In a preferred embodiment of the anti-TROP-2 antibody, antigen-binding fragment thereof or mutant thereof of the present disclosure, wherein:

the anti-TROP-2 antibody, antigen-binding fragment thereof or mutant thereof comprises the heavy chain variable region as shown in SEQ ID NO: 16, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 17, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 18, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 19, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 20, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 31, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 32, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 33, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 34, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same.

In a preferred embodiment of the anti-TROP-2 antibody, antigen-binding fragment thereof or mutant thereof of the present disclosure, wherein:

the anti-TROP-2 antibody or mutant thereof comprises the heavy chain as shown in SEQ ID NO: 21, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 22, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 23, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 24, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 25, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 35, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 36, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 37, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 38, or a heavy chain having at least 80%, 85%, 90%, 95% or 99% identity with the same, and the light chain as shown in SEQ ID NO: 15, or a light chain having at least 80%, 85%, 90%, 95% or 99% identity with the same.

The present disclosure also relates to a polynucleotide encoding the above-mentioned anti-TROP-2 antibody, antigen-binding fragment thereof or mutant thereof.

The present disclosure also relates to an expression vector comprising the above-mentioned polynucleotide.

The present disclosure also relates to a host cell transformed with the above-mentioned expression vector.

The present disclosure also relates to a preferred embodiment, in which the host cell is selected from the group consisting of bacterium, yeast and mammalian cell.

The present disclosure also relates to a further preferred embodiment, in which the host cell is selected from the group consisting of *Escherichia coli, Pichia pastoris*, CHO cell and HEK293 cell.

The present disclosure also relates to a method of producing the above-mentioned anti-TROP-2 antibody, antigen-binding fragment thereof or mutant thereof, the method comprises the following steps: culturing the above-mentioned host cell, preferably HEK293 cells; isolating the antibody from the culture, preferably isolating the antibody from the cell culture fluid; and purifying the antibody, preferably purifying the antibody by chromatographic methods.

The present disclosure also relates to a pharmaceutical composition comprising the above-mentioned anti-TROP-2 antibody, antigen-binding fragment thereof or mutant thereof, as well as a pharmaceutically acceptable excipient, diluent or carrier.

The present disclosure also relates to a detection or diagnostic kit comprising the above-mentioned anti-TROP-2 antibody, antigen-binding fragment thereof or mutant thereof.

The present disclosure also relates to use of the above-mentioned anti-TROP-2 antibody, antigen-binding fragment thereof or mutant thereof in the preparation of a medicament, the medicament is for treating or preventing a TROP-2-mediated disease or condition.

The present disclosure also relates to use of the above-mentioned anti-TROP-2 antibody, antigen-binding fragment thereof or mutant thereof in the preparation of a reagent, wherein the reagent is for detecting, diagnosing and prognosing a TROP-2-mediated disease or condition.

The present disclosure also relates to a preferred embodiment of the above-mentioned use, wherein the TROP-2-mediated disease or condition is a cancer; preferably, the TROP-2-mediated disease or condition is a cancer expressing TROP-2; preferably, the cancer is selected from the group consisting of breast cancer, non-small cell lung cancer, ovarian cancer, prostate cancer, pancreatic cancer, kidney cancer, lung cancer, liver cancer, gastric cancer, colon cancer, bladder cancer, esophageal cancer, cervical cancer, gallbladder cancer, glioblastoma and melanoma.

The present disclosure also relates to a preferred embodiment of the above-mentioned anti-TROP-2 antibody, antigen-binding fragment thereof or mutant thereof, which is used for treating or preventing a TROP-2-mediated disease, the disease is selected from the group consisting of breast cancer, non-small cell lung cancer, ovarian cancer, prostate cancer, pancreatic cancer, kidney cancer, lung cancer, liver cancer, gastric cancer, colon cancer, bladder cancer, esophageal cancer, cervical cancer, gallbladder cancer, glioblastoma and melanoma.

The present disclosure also relates to a preferred embodiment of the above-mentioned anti-TROP-2 antibody, antigen-binding fragment thereof or mutant thereof, which is used for detecting, diagnosing and prognosing a TROP-2-mediated disease, the disease is selected from the group consisting of breast cancer, non-small cell lung cancer, ovarian cancer, prostate cancer, pancreatic cancer, kidney cancer, lung cancer, liver cancer, gastric cancer, colon cancer, bladder cancer, esophageal cancer, cervical cancer, gallbladder cancer, glioblastoma and melanoma.

The present disclosure also relates to a method of treating or preventing a TROP-2-mediated disease, comprising the following steps: providing to a subject in need a therapeutically or prophylactically effective amount of the anti-TROP-2 antibody, antigen-binding fragment thereof or mutant thereof as described above, or providing to a subject in need a therapeutically or prophylactically effective amount of the pharmaceutical composition according to the present disclosure, wherein the TROP-2-mediated disease is selected from the group consisting of breast cancer, non-small cell lung cancer, ovarian cancer, prostate cancer, pancreatic cancer, kidney cancer, lung cancer, liver cancer, gastric cancer, colon cancer, bladder cancer, esophageal cancer, cervical cancer, gallbladder cancer, glioblastoma and melanoma.

DETAILED DESCRIPTION OF THE INVENTION

Terms

For easier understanding of the present disclosure, certain technical and scientific terms are specifically defined below. Unless otherwise clearly defined elsewhere in this document, all other technical and scientific terms used herein have the meanings commonly understood by those of ordinary skilled in the art to which the present disclosure belongs.

The three-letter codes and one-letter codes of amino acids used in the present disclosure are as described in J. Biol. Chem, 243, p 3558 (1968).

The term "antibody" described in the present disclosure refers to an immunoglobulin, which is a tetra-peptide chain structure composed of two heavy chains and two light chains linked by interchain disulfide bonds. The amino acid composition and order of arrangement of the immunoglobulin heavy chain constant regions are different, so their antigenicity is also different. Accordingly, immunoglobulins can be classified into five types, or immunoglobulin isotypes, namely IgM, IgD, IgG, IgA and IgE, and their corresponding heavy chains are μ chain, δ chain, γ chain, α chain and ε chain, respectively. The same type of Ig can be classified into different subclasses according to the difference in the amino acid composition of the hinge region and the number and position of heavy chain disulfide bonds. For example, IgG can be classified into IgG1, IgG2, IgG3 and IgG4. The light chain is classified into κ chain or λ chain according to the difference in the constant region. Each of the five types of Ig can have a κ chain or a λ chain.

In the present disclosure, the antibody light chain can further comprise a light chain constant region, which comprises human or murine κ, λ chain or a variant thereof.

In the present disclosure, the antibody heavy chain can further comprise a heavy chain constant region, which comprises human or murine IgG1, IgG2, IgG3, IgG4 or a variant thereof.

The sequence of about 110 amino acids near the N-terminus of the antibody heavy and light chains varies greatly and is named as variable region (V region); the rest amino acid sequence near the C-terminus is relatively stable and is named as constant region (C region). The variable region comprises 3 hypervariable regions (HVRs) and 4 framework regions (FRs) with relatively conservative sequences. The 3 hypervariable regions determine the specificity of the antibody, and are also known as complementarity determining regions (CDR). Each light chain variable region (VL) and heavy chain variable region (VH) consists of 3 CDR regions and 4 FR regions, arranged from the amino terminus to the carboxyl terminus in the order of FR1, CDR1, FR2, CDR2, FR3, CDR3, FR4. The 3 CDR regions of the light chain refer to LCDR1, LCDR2 and LCDR3; the 3 CDR regions of the heavy chain refer to HCDR1, HCDR2 and HCDR3. The number and position of the CDR amino acid residues of the VL region and VH region of the antibody or antigen-binding fragment according to the present disclosure comply with the known Kabat numbering and Kabat or ABM criteria.

The term "TROP-2" includes any naturally expressed variant or isoform of TROP-2. The antibody of the present disclosure can cross-react with TROP-2 derived from non-human species. As an alternative, the antibody can also be specific for human TROP-2 and may not show cross-reactivity with other species. TROP-2 or any variant or isoform thereof can be isolated from cells or tissues naturally expressing them, or produced by recombinant techniques using the techniques commonly used in the art and those described herein. Preferably, the anti-TROP-2 antibody targets human TROP-2 that has a normal glycosylation pattern.

The term "recombinant human antibody" includes human antibodies prepared, expressed, created or isolated by recombinant methods, and the techniques and methods involved are well known in the art, such as:

1. antibodies isolated from transgenic and transchromosomal animals (for example mice) of human immunoglobulin genes, or hybridomas prepared therefrom;
2. antibodies isolated from host cells transformed to express the antibodies, such as transfectionomas;
3. antibodies isolated from recombinant combinatorial human antibody libraries; and
4. antibodies prepared, expressed, created or isolated by techinques such as splicing human immunoglobulin gene sequences into other DNA sequences.

Such recombinant human antibodies comprise variable regions and constant regions, which utilize specific human germline immunoglobulin sequences encoded by germline genes, but also comprise subsequent rearrangements and mutations such as those occur during antibody maturation.

The term "murine antibody" in the present disclosure is a monoclonal antibody against human TROP-2 according to the knowledge and skills in the art. During preparation, the test subject is injected with TROP-2 antigen, and then hybridomas expressing antibodies with the desired sequence or functional properties are isolated. In an exemplary embodiment of the present disclosure, the murine TROP-2 antibody or antigen-binding fragment thereof may further comprise the light chain constant region of murine κ, λ chain or a variant thereof, or further comprise the heavy chain constant region of murine IgG1, IgG2, IgG3 or IgG4 or a variant thereof.

The term "human antibody" includes antibodies with variable and constant regions of human germline immunoglobulin sequences. The human antibodies of the present disclosure may include amino acid residues that are not encoded by human germline immunoglobulin sequences (such as mutations introduced by random or site-specific mutagenesis in vitro or by somatic mutations in vivo). However, the term "human antibody" does not include humanized antibodies.

The term "humanized antibody", also known as CDR-grafted antibody, refers to an antibody produced by grafting the CDR sequences of non-human species into the framework of human antibody variable regions. Humanized antibodies can overcome the shortcomings of strong immune responses induced by chimeric antibodies due to the large amount of non-human protein components they carry. In order to avoid the decrease in activity caused by the decrease in immunogenicity, the human antibody variable regions can be subjected to minimal reverse mutation to maintain the activity.

The term "chimeric antibody" is an antibody formed by fusing the antibody variable region of the first species with the antibody constant region of the second species, which can alleviate the immune response induced by an antibody of the first species. As an example, establishing a chimeric antibody requires first establishing a hybridoma that secrets a murine specific monoclonal antibody, then cloning the variable region gene from a murine hybridoma cell, and then cloning the constant region gene of a human antibody as necessary, and linking the murine variable region gene to the human constant region gene to form a chimeric gene, which is inserted into a human expression vector, and finally expressing the chimeric antibody molecule in a eukaryotic industrial system or a prokaryotic industrial system. The constant region of the human antibody can be selected from the heavy chain constant regions of human IgG1, IgG2, IgG3 and IgG4 and variants thereof, preferably comprising a human IgG1, IgG2 or IgG4 heavy chain constant region, or using an IgG1 heavy chain constant region with enhanced ADCC (antibody-dependent cell-mediated cytotoxicity) toxicity after amino acid mutation.

The term "antigen-binding fragment" refers to an antigen-binding fragment of an antibody and an antibody analog, which usually comprises at least part of the antigen-binding region or variable region (for example one or more CDR(s)) of the parental antibody. The antibody fragment retains at least some of the binding specificity of the parental antibody. Typically, when the activity is represented on a mole basis, the antibody fragment retains at least 10% binding activity of the parental antibody. Preferably, the antibody fragment retains at least 20%, 50%, 70%, 80%, 90%, 95% or 100% or more of the binding affinity of the parental antibody to the target. Examples of antigen-binding fragments include, but are not limited to, Fab, Fab', F(ab')2, Fv fragment, linear antibody, single-chain antibody, nanobody, domain antibody and multispecific antibody. Engineered antibody variants are reviewed in Holliger and Hudson, 2005, Nat. Biotechnol. 23: 1126-1136.

The "Fab fragment" consists of one light chain and the CH1 and the variable region of one heavy chain. The heavy chain of a Fab molecule cannot form disulfide bonds with another heavy chain molecule.

The "Fc" region contains two heavy chain fragments comprising the CH1 and CH2 domains of the antibody. The two heavy chain fragments are held together by two or more disulfide bonds and through the hydrophobic interaction of the CH3 domain.

The "Fab' fragment" contains one light chain and a part of one heavy chain comprising the VH domain, the CH1 domain and the region between the CH1 and CH2 domains, so that interchain disulfide bonds can be formed between the two heavy chains of two Fab' fragments, thereby forming a F(ab')2 molecule.

The "F(ab')2 fragment" contains two light chains and two heavy chains comprising a part of the constant region between the CH1 and CH2 domains, thereby forming interchain disulfide bonds between the two heavy chains. Therefore, the F(ab')2 fragment consists of two Fab' fragments held together by disulfide bonds between the two heavy chains.

The "Fv region" comprises variable regions from both the heavy chain and the light chain, but lacks constant regions.

The term "multispecific antibody" is used in its broadest sense, encompassing antibodies with multi-epitope specificity. These multispecific antibodies include, but are not limited to: antibodies comprising heavy chain variable region VH and light chain variable region VL, wherein the VH-VL unit has multi-epitope specificity; antibodies with two or more VL and VH regions, each VH-VL unit binds to a different target or a different epitope of the same target; antibodies with two or more single variable regions, each single variable region binds to a different target or a different epitope of the same target; full-length antibodies, antibody fragments, diabodies, bispecific diabodies and triabodies, covalently or non-covalently linked antibody fragments, and the like.

The term "single-chain antibody" is a single-chain recombinant protein formed by linking the heavy chain variable region VH and light chain variable region VL of an antibody through a linker peptide. It is the minimum antibody fragment with intact antigen binding site.

The term "domain antibody fragment" is an immunoglobulin fragment that contains only the heavy chain variable region or the light chain variable region and has immunological functions. In certain cases, two or more VH regions are covalently linked by peptide linkers to form a bivalent domain antibody fragment. The two VH regions of the bivalent domain antibody fragment can target the same antigen or different antigens.

The term "bind to TROP-2" refers to the ability to interact with TROP-2 or an epitope thereof.

The term "antigen-binding site" refers to a three-dimensional site recognized by the antibody or antigen-binding fragment of the present disclosure.

The term "epitope" refers to a site on an antigen that specifically binds to an immunoglobulin or antibody. Epitopes can be formed by adjacent amino acids or by non-adjacent amino acids by tertiary folding of the protein. Epitopes formed by adjacent amino acids are usually maintained after exposure to a denaturing solvent, while epitopes formed by tertiary folding are usually lost after treatment with a denaturing solvent. Epitopes usually comprise at least 3-15 amino acids in a unique spatial conformation. Methods for determining what epitope is bound to a given antibody are well known in the art, including immunoblotting, immunoprecipitation detection analysis and the like. Methods for determining the spatial conformation of an epitope include the techniques in the art and the techniques described herein, for example X-ray crystallography analysis, two-dimensional nuclear magnetic resonance and the like.

The terms "specific binding" and "selective binding" refer to the binding of an antibody to an epitope on a predetermined antigen. Typically, when recombinant human TROP-2 is used as the analyte and an antibody is used as the ligand, when measured by surface plasmon resonance (SPR) technology in an instrument, the antibody binds to the predetermined antigen (or epitope) at an equilibrium dissociation constant ($K_D$) of about less than $10^{-7}$ M or even less, and its binding affinity to the predetermined antigen (or epitope) is at least two times higher than that for non-specific antigens other than the predetermined antigen or closely related antigens, such as BSA and the like. The term "antigen-recognizing antibody" can be used interchangeably with the term "specific binding antibody" herein.

The term "cross-reaction" refers to the ability of the antibody of the present disclosure to bind to TROP-2 from different species. For example, an antibody of the present disclosure that binds to human TROP-2 can also bind to TROP-2 of another species. Cross-reactivity is measured by detecting the specific reactivity with purified antigen or the binding to or the functional interaction with cells that physiologically express TROP-2 in binding assays (for example SPR and ELISA). Methods for determining cross-reactivity include standard binding assays as described herein, for example surface plasmon resonance (SPR) analysis or flow cytometry.

The terms "inhibition" or "blocking" can be used interchangeably and encompass both partial and complete inhibition/blocking. Preferably, compared to the normal level or type of activity when there is no inhibition or blocking, inhibition or blocking of a ligand reduces or alters the level or type of activity. Inhibition and blocking are also intended to include any measurable reduction in binding affinity to the ligand when in contact with anti-TROP-2 antibody, compared to the ligand not in contact with anti-TROP-2 antibody.

The term "inhibition of growth" (for example involving cells) is intended to include any measurable reduction in cell growth.

The terms "induced immune response" and "enhanced immune response" can be used interchangeably and refer to the immune response stimulated (i.e. passive or adaptive) by a specific antigen. The term "induce" for inducing CDC or ADCC refers to stimulating a specific direct cell killing mechanism.

The term "ADCC", i.e. antibody-dependent cell-mediated cytotoxicity, means that a cell expressing Fc receptors directly kills a target cell targeted by an antibody by recognizing the Fc fragment of the antibody. The ADCC effector function of an antibody can be enhanced, reduced or eliminated by modifying the Fc fragment of IgG. The modification refers to mutation in the heavy chain constant region of the antibody.

The methods for producing and purifying antibodies and antigen-binding fragments are well-known and can be found in the prior art, such as Antibodies: A Laboratory Manual, Cold Spring Harbor, chapters 5-8 and 15. As an example, human TROP-2 or fragment thereof can be used to immunize mice, and the obtained antibodies can be renatured, purified and subjected to amino acid sequencing by conventional methods. Similarly, antigen-binding fragments can also be prepared by conventional methods. One or more human FR regions are added to non-human CDR regions by genetic engineering to obtain the antibody or antigen-binding fragment of the present invention. The human FR germline sequences can be obtained from the ImMunoGeneTics (IMGT) or from The Immunoglobulin FactsBook, 2001ISBN012441351.

The engineered antibodies or antigen-binding fragments of the present disclosure can be prepared and purified by conventional methods. The cDNA sequences of the corresponding antibodies can be cloned and recombined into GS expression vectors. The recombinant immunoglobulin expression vectors can stably transfect CHO cells. As a more recommended prior art, mammalian expression systems can lead to glycosylation of antibodies, especially at the highly conserved N-terminus of the Fc region. Stable clones are obtained by expressing antibodies that specifically bind to human antigens. Positive clones are expanded in serum-free medium in bioreactors to produce the antibodies. The culture fluid into which the antibodies are secreted can be purified and collected by conventional techniques. The antibodies can be filtered and concentrated by conventional methods. Soluble mixtures and multimers can also be removed by conventional methods, for example molecular sieves and ion exchange. The resulting product needs to be frozen immediately, such as at −70° C., or lyophilized.

The antibody of the present disclosure refers to monoclonal antibody. The monoclonal antibody (mAb) as described the present disclosure refers to an antibody obtained from a monoclonal cell strain, which is not limited to eukaryotic, prokaryotic or phage clonal cell strains. Monoclonal antibodies or antigen-binding fragments can be obtained by recombination using, for example, hybridoma technology, recombination technology, phage display technology, synthesis technology (such as CDR-grafting) or other existing technologies.

"Administration", "dosing" and "treatment", when applied to an animal, a human, an experimental subject, a cell, a tissue, an organ or a biological fluid, refer to contacting an exogenous medicament, a therapeutic agent, a diagnostic agent or a composition with the animal, human, subject, cell, tissue, organ or biological fluid. "Administration", "dosing" and "treatment" can refer to, for example, treatment, pharmacokinetics, diagnostic, research and experimental methods. Treatment of a cell includes contacting a reagent with the cell, and contacting the reagent with a fluid, wherein the fluid is in contact with the cell. "Administration", "dosing" and "treatment" also refer to treating, for example a cell, by a reagent, diagnostic, a binding composition or by another cell in vitro and ex vivo. "Administration", "dosing" and "treatment", when applied to a human, a veterinary or research subject, refer to therapeutic treatment, preventive or prophylactic measures, research and diagnostic applications.

"Treatment" refers to providing an internal or external therapeutic agent (for example agent comprising any one of the antibodies or a fragment thereof of the present disclosure) to a subject having one or more disease symptoms on which the therapeutic agent is known to have therapeutic effect. Typically, the therapeutic agent is given at an amount effective to alleviate one or more disease symptoms in the subject or subject population being treated, either to induce the regression of such symptoms, or to suppress the progression of such symptoms to any clinically measurable extent. The amount of therapeutic agent effective to alleviate any specific disease symptom (also referred to as a "therapeutically effective amount") can vary depending on a variety of factors, for example the subject's disease state, age and body weight, and the ability of the drug to produce the desired therapeutic effect in the subject. Whether the disease symptom has been alleviated can be evaluated by any clinical testing method commonly used by doctors or other health care professionals for evaluating the severity or progression of the symptom. Although the embodiments of the present disclosure (for example a treatment method or a product) may not be effective in alleviating the target disease symptom in every subject, but as determined according to any statistical test methods known in the art such as Student t test, chi-square test, Mann and Whitney's U test, Kruskal-Wallis test (H test), Jonckheere-Terpstra test and Wilcoxon test, they should significantly reduce the target disease symptom in a statistically effective number of subjects.

The "effective amount" includes an amount sufficient to ameliorate or prevent a medical condition or a symptom thereof. The effective amount also refers to an amount sufficient to allow or facilitate diagnosis. The effective amount for a particular subject or veterinary subject can vary depending on the following factors, such as, the condition to be treated, the general health condition of the subject, the method, route and dosage of dosing, and the severity of side effects. The effective amount can be the maximum dose or dosing regimen that avoids significant side effects or toxic effects.

"Exogenous" refers to substances produced outside organisms, cells or human bodies depending on backgrounds.

"Endogenous" refers to substances produced inside cells, organisms or human bodies depending on backgrounds.

"Homology" or "identity" refers to the sequence similarity between two polynucleotide sequences or between two polypeptides. When the positions in the two sequences aligned are occupied by the same base or amino acid residue, for example if each position of two DNA molecules is occupied by adenine, then the molecules are homologous at that position. The homology percentage between two sequences is a function of the number of matched or homologous positions shared among the two sequences divided by the number of positions aligned×100%. For example, in the optimal sequence alignment, if 6 out of 10 positions in the two sequences are matched or homologous, then the two sequences are 60% homologous. Generally, the alignment is made when two sequences are aligned to obtain the maximum homology percentage.

The expressions "cell", "cell line" and "cell culture" used herein can be used interchangeably, and all such names include progenies thereof. Therefore, the expressions "transformant" and "transformed cell" include primary cells and cultures derived therefrom, regardless of the number of passages. It should also be understood that due to intentional or unintentional mutations, it is impossible that all progenies are exactly the same in terms of DNA content. Mutant progenies with the same function or biological activity as screened in the primary cells are included. It can be clearly seen from the context when different names are referred to.

"Optional" or "optionally" means that the event or circumstance described subsequently can occur but need not occur, and the description includes the cases in which the event or circumstance occurs or does not occur. For example, "optionally comprising 1 to 3 antibody heavy chain variable regions" means that the antibody heavy chain variable regions of particular sequences can but need not be present.

The "pharmaceutical composition" means it contains one or more antibodies or antigen-binding fragments described herein as well as other components such as physiological/pharmaceutically acceptable carriers and excipients. The objective of the pharmaceutical composition is to facilitate drug administration to an organism, and to benefit the absorption of the active ingredient so as to exert the biological activity.

In the context, if not clearly indicated, the singular form "a/an", "one" or "the" also includes its corresponding plural form.

The present disclosure will be further described with reference to the following examples, but the examples should not be considered as limiting the scope of the present disclosure. The experimental methods without specified conditions in the examples of the present disclosure usually follow conventional conditions, such as those in Antibodies: A Laboratory Manual and Molecular Cloning: A Laboratory Manual, Cold Spring Harbor; or according to the conditions recommended by the raw material or product manufacturer. The reagents without specified sources are conventional reagents purchased from the market.

Example 1: Preparation of Antigens

The protein encoding the His-tagged human TROP-2 (TROP-2-His) was synthesized by SinoBiologics (10428-H08H).

```
The sequence of TROP-2-His:
                                              SEQ ID NO: 1
MARGPGLAPPPLRLPLLLLVLAAVTGHTAAQDNCTCPTNKMTVCSPDGP

GGRCQCRALGSGMAVDCSTLTSKCLLLKARMSAPKNARTLVRPSEHALV

DNDGLYDPDCDPEGRFKARQCNQTSVCWCVNSVGVRRTDKGDLSLRCDE

LVRTHHILIDLRHRPTAGAFNHSDLDAELRRLFRERYRLHPKFVAAVHY

EQPTIQIELRQNTSQKAAGDVDIGDAAYYFERDIKGESLFQGRGGLDLR

VRGEPLQVERTLIYYLDEIPPKFSMKRLTAGLIAVIVVVVVALVAGMAV

LVITNRRKSGKYKKVEIKELGELRKEPSLHHHHHHHH.
```

Example 2: Obtaining Murine Hybridomas and Antibody Sequences

A total of 5 Balb/c and 5 A/J female 10-week-old mice were immunized with the human antigen TROP-2-His. Sigma Complete Freund's Adjuvant (CFA) and Sigma Incomplete Freund's Adjuvant (IFA) were used. The immunogen and the immune adjuvant were thoroughly mixed at a ratio of 1:1 and emulsified to make a stable "water-in-oil" liquid. The injection dose was 25 g/200 L/mouse.

TABLE 1

| Immunization scheme | |
|---|---|
| Day 1 | First immunization, complete Freund's adjuvant. |
| Day 21 | Second immunization, incomplete Freund's adjuvant. |
| Day 35 | Third immunization, incomplete Freund's adjuvant. |
| Day 42 | Blood sampling and serum titer test (blood after 3 immunizations) |
| Day 49 | Fourth immunization, incomplete Freund's adjuvant. |
| Day 56 | Blood sampling and serum titer test (blood after 4 immunizations) |

As for the serum of immunized mice, the serum titer and the ability to bind to cell surface antigens were evaluated by using indirect ELISA as described in Example 3. The initiation of cell fusion was determined according to the detection results of titer (greater than 100,000-fold dilution). The immunized mice with high serum titer, affinity and Fluorescence-Activated Cell Sorting binding were selected for one final immunization and then sacrificed. The spleen cells were collected, fused with SP2/0 myeloma cells and plated to obtain hybridomas. The target hybridomas were screened by indirect ELISA and established as monoclonal cell strains by limiting dilution method. The obtained positive antibody strains were further screened by indirect ELISA so as to select the hybridomas that bound to the recombinant protein. Hybridoma cells at logarithmic growth phase were collected. RNA was extracted with TRIZOL™ (Invitrogen, 15596-018) and subjected to reverse transcription (PRIMESCRIPT™ Reverse Transcriptase, Takara #2680A). The cDNA obtained by reverse transcription was amplified by PCR using a mouse Ig-primer set (Novagen, TB326 Rev.B 0503) and subjected to sequencing to finally obtain the sequence of the murine antibody.

The sequences of the heavy chain and light chain variable regions of murine monoclonal antibody M1 are as follows:

M1 HCVR

SEQ ID NO: 2

QVQLQQPGAELVRPGASVKLSCRASGYTFTNYWMNWVKQRPEQGLEWIG

RIDPNDSETHYNQKFKDRAILTVDKASNTAYMQLSGLTSEDSAVHYCAR

SGFGSTYWFFDVWGAGTTVTVSS

M1 LCVR

SEQ ID NO: 3

DIVMTQSHKFMSTSVGDRVSITCKASQDVSTAVAWYQQKPGQSPKLLIY

SASYRYTGVPDRFAGSGYGTDFTFTISSVQTEDLTVYHCQQHYSTPLTF

GPGTRLELK.

TABLE 2

The CDR sequences of the heavy chain and light chain variable regions of murine monoclonal antibody M1

| Name | Sequence | No. |
|---|---|---|
| HCDR1 | NYWMN | SEQ ID NO: 4 |
| HCDR2 | RIDPNDSETHYNQKFKD | SEQ ID NO: 5 |
| HCDR3 | SGFGSTYWFFDV | SEQ ID NO: 6 |
| LCDR1 | KASQDVSTAVA | SEQ ID NO: 7 |
| LCDR2 | SASYRYT | SEQ ID NO: 8 |
| LCDR3 | QQHYSTPLT | SEQ ID NO: 9 |

Examples 3: Detection Method for In Vitro Binding Activity of Antibodies

In Vitro Indirect ELISA Binding Experiment:

TROP-2 His protein (Sino Biological Inc., cat #10428-H08H) was diluted with pH 7.4 PBS to a concentration of 1 μg/ml, added to a 96-well high-affinity ELISA plate at 100 μl/well and incubated in a refrigerator at 4° C. overnight (16-20 hours). After washing the plate 4 times with PBST (pH 7.4 PBS comprising 0.05% Tween-20™), 3% bovine serum albumin (BSA) blocking solution diluted with PBST was added at 150 μl/well and incubated at room temperature for 1 hour for blocking. After completion of the blocking, the blocking solution was discarded, and the plate was washed 4 times with PBST buffer.

The antibody to be tested was diluted with PBST comprising 3% BSA to obtain a series of 5-fold dilutions (with 9 doses in total, starting from 10 μM), and was added to the ELISA plate at 100 μl/well, and incubated at room temperature for 1 hour. After completion of the incubation, the plate was washed 4 times with PBST. HRP-labeled goat-anti-human secondary antibody (Abcam, cat #ab97225) diluted with PBST comprising 3% BSA was added at 100 μl/well and incubated at room temperature for 1 hour. The plate was washed 4 times with PBST, then TMB chromogenic substrate (Cell Signaling Technology, cat #7004S) was added at 100 μl/well and incubated at room temperature in the dark for 1 minute. The stop solution (Cell Signaling Technology, cat #7002S) was added at 100 μl/well to terminate the reaction. The absorbance at 450 nm was read with a microplate reader (BioTek, model Synergy H1) and the data were analyzed. The results were analyzed by plotting the concentration-signal curve, as shown in Table 3 below:

TABLE 3

Affinity of murine antibodies to human TROP-2 antigen ($EC_{50}$ value)

| Murine antibody | $EC_{50}$ representing the binding to human TROP-2 His antigen (nM) |
|---|---|
| M1 | 0.56 |

Example 4: Humanization Experiment of Murine Antibodies

Humanization of the murine anti-human TROP-2 monoclonal antibodies was performed by using methods as disclosed in many literatures in the art. Briefly, parental (murine antibody) constant domains were replaced with human constant domains. Human germline antibody sequences were selected according to the homology of the murine antibody and human antibody. The murine antibody M1 was humanized in the present disclosure.

On the basis of the typical structure of the VH/VL CDR of the obtained murine antibody, the sequences of heavy and light chain variable regions were aligned with the human antibody germline database to obtain human germline templates with high homology.

The CDR regions of the murine antibody M1 were grafted onto the selected corresponding humanizing templates. Then, based on the three-dimensional structure of the murine antibody, the embedded residues, the residues directly interacting with the CDR regions and the residues with significant influence on the conformation of VL and VH were subjected to back mutation. After expression test and comparison of the number of back mutations, the antibody designed by combining humanized heavy chain variable region HCVR and light chain variable region LCVR sequences was selected, and the sequences are as follows:

HU6 HCVR

SEQ ID NO: 10

EVQLLESGGGLVQPGGSLRLSCAASGFTVSNYWMNWVRQAPGKGLEWMG

RIDPNDSETHYNQKFKDRVTISVDKSKNQFSLKLSSVTAADTAVYYCAR

SGFGSTYWFFDVWGQGTTVTVSS

HU6 LCVR

SEQ ID NO: 11

DVVMTQSPLSLPVTLGQPASISCKASQDVSTAVAWYQQKPGKAPKLFIY

SASYRYTGVPSRFSGSGSGTDFTLTISSLQPEDFATYYCQQHYSTPLTF

GQGTRLEIK.

The designed sequences of heavy chain and light chain variable regions were linked to the sequences of IgG1 heavy chain and light chain constant regions respectively. The sequence of the linked human IgG1 heavy chain constant region is as follows:

```
IgG1 C1
                                          SEQ ID NO: 12
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK;
```

the designed sequences of heavy chain and light chain variable regions were linked to the sequences of IgG1 heavy chain and light chain constant regions respectively. The sequence of the linked human kappa chain constant region is as follows:

```
Ig kappa C
                                          SEQ ID NO: 13
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC;
```

exemplary heavy chain and light chain sequences obtained after linking are as follows:

```
HU6DL HC
                                          SEQ ID NO: 14
EVQLLESGGGLVQPGGSLRLSCAASGFTVSNYWMNWVRQAPGKGLEWMG

RIDPNDSETHYNQKFKDRVTISVDKSKNQFSLKLSSVTAADTAVYYCAR
```

-continued

```
SGFGSTYWFFDVWGQGTTVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLSLSPGK

HU6DL LC
                                          SEQ ID NO: 15
DVVMTQSPLSLPVTLGQPASISCKASQDVSTAVAWYQQKPGKAPKLFIY

SASYRYTGVPSRFSGSGSGTDFTLTISSLQPEDFATYYCQQHYSTPLTF

GQGTRLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.
```

Example 5: HU6DL Variant Design Experiment

The humanized antibody HU6DL has an $N^{54}D^{55}S^{56}$ motif in HCDR2 and is susceptible to glycosylation. N54 was subjected to site-directed mutation by computer-aided technology to reduce the potential risk of glycosylation without affecting its binding to antigen and its own thermostability. The mutants of antibody HU6DL, namely HU6DL.R54, HU6DL.Y54, HU6DL.Q54, HU6DL.L54, HU6DL.T54, HU6DL.154, HU6DL.F54, HU6DL.E54 and HU6DL.A54, were obtained, and the corresponding heavy chain and light chain variable regions are as follows:

```
HU6DL.R54 HCVR
                                                   SEQ ID NO: 16
EVQLLESGGGLVQPGGSLRLSCAASGFTVSNYWMNWVRQAPGKGLEWMGRID

PRDSETHYNQKFKDRVTISVDKSKNQFSLKLSSVTAADTAVYYCARSGFGSTYW

FFDVWGQGTTVTVSS

HU6DL.R54 LCVR
                                                   SEQ ID NO: 11
DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIK

HU6DL.Y54 HCVR
                                                   SEQ ID NO: 17
EVQLLESGGGLVQPGGSLRLSCAASGFTVSNYWMNWVRQAPGKGLEWMGRID

PYDSETHYNQKFKDRVTISVDKSKNQFSLKLSSVTAADTAVYYCARSGFGSTYW

FFDVWGQGTTVTVSS

HU6DL.Y54 LCVR
                                                   SEQ ID NO: 11
DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIK
```

-continued

HU6DL.Q54 HCVR

SEQ ID NO: 18

EVQLLESGGGLVQPGGSLRLSCAASGFTVSNYWMNWVRQAPGKGLEWMGRID

PQDSETHYNQKFKDRVTISVDKSKNQFSLKLSSVTAADTAVYYCARSGFGSTYW

FFDVWGQGTTVTVSS

HU6DL.Q54 LCVR

SEQ ID NO: 11

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIK

HU6DL.L54 HCVR

SEQ ID NO: 19

EVQLLESGGGLVQPGGSLRLSCAASGFTVSNYWMNWVRQAPGKGLEWMGRID

PLDSETHYNQKFKDRVTISVDKSKNQFSLKLSSVTAADTAVYYCARSGFGSTYW

FFDVWGQGTTVTVSS

HU6DL.L54 LCVR

SEQ ID NO: 11

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIK

HU6DL.T54 HCVR

SEQ ID NO: 20

EVQLLESGGGLVQPGGSLRLSCAASGFTVSNYWMNWVRQAPGKGLEWMGRID

PTDSETHYNQKFKDRVTISVDKSKNQFSLKLSSVTAADTAVYYCARSGFGSTYW

FFDVWGQGTTVTVSS

HU6DL.T54 LCVR

SEQ ID NO: 11

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIK

HU6DL.I54 HCVR

SEQ ID NO: 31

EVQLLESGGGLVQPGGSLRLSCAASGFTVSNYWMNWVRQAPGKGLEWMGRID

PIDSETHYNQKFKDRVTISVDKSKNQFSLKLSSVTAADTAVYYCARSGFGSTYW

FFDVWGQGTTVTVSS

HU6DL.I54 LCVR

SEQ ID NO: 11

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIK

HU6DL.F54 HCVR

SEQ ID NO: 32

EVQLLESGGGLVQPGGSLRLSCAASGFTVSNYWMNWVRQAPGKGLEWMGRID

PFDSETHYNQKFKDRVTISVDKSKNQFSLKLSSVTAADTAVYYCARSGFGSTYW

FFDVWGQGTTVTVSS

HU6DL.F54 LCVR

SEQ ID NO: 11

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIK

HU6DL.E54 HCVR

SEQ ID NO: 33

EVQLLESGGGLVQPGGSLRLSCAASGFTVSNYWMNWVRQAPGKGLEWMGRID

PEDSETHYNQKFKDRVTISVDKSKNQFSLKLSSVTAADTAVYYCARSGFGSTYW

FFDVWGQGTTVTVSS

-continued

HU6DL.E54 LCVR

SEQ ID NO: 11

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIK

HU6DL.A54 HCVR

SEQ ID NO: 34

EVQLLESGGGLVQPGGSLRLSCAASGFTVSNYWMNWVRQAPGKGLEWMGRID

PADSETHYNQKFKDRVTISVDKSKNQFSLKLSSVTAADTAVYYCARSGFGSTYW

FFDVWGQGTTVTVSS

HU6DL.A54 LCVR

SEQ ID NO: 11

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIK.

The designed sequences of heavy chain and light chain variable regions were linked to the sequences of IgG1 heavy chain constant region and light chain constant region respectively. Exemplary heavy chain and light chain sequences obtained are as follows (wherein, HU6DL.R54, HU6DL.Y54, HU6DL.Q54, HU6DL.L54, HU6DL.T54, HU6DL.154, HU6DL.F54, HU6DL.E54 and HU6DL.A54 heavy chains result from linking the sequences SEQ ID NO: 16, SEQ ID NO: 17, SEQ ID NO: 18, SEQ ID NO: 19, SEQ ID NO: 20, SEQ ID NO: 31, SEQ ID NO: 32, SEQ ID NO: 33, and SEQ ID NO: 34 to the sequence SEQ ID NO: 12 respectively):

HU6DL.R54 HC

SEQ ID NO: 21

EVQLLESGGGLVQPGGSLRLSCAASGFTVSNYWMNWVRQAPGKGLEWMGRID

PRDSETHYNQKFKDRVTISVDKSKNQFSLKLSSVTAADTAVYYCARSGFGSTYW

FFDVWGQGTTVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSV

MHEALHNHYTQKSLSLSPGK

HU6DL.R54 LC

SEQ ID NO: 15

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIKRTV

AAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC

HU6DL.Y54 HC

SEQ ID NO: 22

EVQLLESGGGLVQPGGSLRLSCAASGFTVSNYWMNWVRQAPGKGLEWMGRID

PYDSETHYNQKFKDRVTISVDKSKNQFSLKLSSVTAADTAVYYCARSGFGSTYW

FFDVWGQGTTVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSV

MHEALHNHYTQKSLSLSPGK

-continued

HU6DL.Y54 LC

SEQ ID NO: 15

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIKRTV

AAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC

HU6DL.Q54 HC

SEQ ID NO: 23

EVQLLESGGGLVQPGGSLRLSCAASGFTVSNYWMNWVRQAPGKGLEWMGRID

PQDSETHYNQKFKDRVTISVDKSKNQFSLKLSSVTAADTAVYYCARSGFGSTYW

FFDVWGQGTTVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSV

MHEALHNHYTQKSLSLSPGK

HU6DL.Q54 LC

SEQ ID NO: 15

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIKRTV

AAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC

HU6DL.L54 HC

SEQ ID NO: 24

EVQLLESGGGLVQPGGSLRLSCAASGFTVSNYWMNWVRQAPGKGLEWMGRID

PLDSETHYNQKFKDRVTISVDKSKNQFSLKLSSVTAADTAVYYCARSGFGSTYW

FFDVWGQGTTVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSV

MHEALHNHYTQKSLSLSPGK

HU6DL.L54 LC

SEQ ID NO: 15

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIKRTV

AAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC

HU6DL.T54 HC

SEQ ID NO: 25

EVQLLESGGGLVQPGGSLRLSCAASGFTVSNYWMNWVRQAPGKGLEWMGRID

PTDSETHYNQKFKDRVTISVDKSKNQFSLKLSSVTAADTAVYYCARSGFGSTYW

FFDVWGQGTTVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKV

-continued

DKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSV

MHEALHNHYTQKSLSLSPGK

HU6DL.T54 LC

SEQ ID NO: 15

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIKRTV

AAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC

HU6DL.I54 HC

SEQ ID NO: 35

EVQLLESGGGLVQPGGSLRLSCAASGFTVSNYWMNWVRQAPGKGLEWMGRID

PIDSETHYNQKFKDRVTISVDKSKNQFSLKLSSVTAADTAVYYCARSGFGSTYW

FFDVWGQGTTVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSV

MHEALHNHYTQKSLSLSPGK

HU6DL.I54 LC

SEQ ID NO: 15

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIKRTV

AAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC

HU6DL.F54 HC

SEQ ID NO: 36

EVQLLESGGGLVQPGGSLRLSCAASGFTVSNYWMNWVRQAPGKGLEWMGRID

PFDSETHYNQKFKDRVTISVDKSKNQFSLKLSSVTAADTAVYYCARSGFGSTYW

FFDVWGQGTTVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSV

MHEALHNHYTQKSLSLSPGK

HU6DL.F54 LC

SEQ ID NO: 15

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIKRTV

AAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC

-continued

HU6DL.E54 HC

SEQ ID NO: 37

EVQLLESGGGLVQPGGSLRLSCAASGFTVSNYWMNWVRQAPGKGLEWMGRID

PEDSETHYNQKFKDRVTISVDKSKNQFSLKLSSVTAADTAVYYCARSGFGSTYW

FFDVWGQGTTVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSV

MHEALHNHYTQKSLSLSPGK

HU6DL.E54 LC

SEQ ID NO: 15

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIKRTV

AAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC

HU6DL.A54 HC

SEQ ID NO: 38

EVQLLESGGGLVQPGGSLRLSCAASGFTVSNYWMNWVRQAPGKGLEWMGRID

PADSETHYNQKFKDRVTISVDKSKNQFSLKLSSVTAADTAVYYCARSGFGSTYW

FFDVWGQGTTVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSV

MHEALHNHYTQKSLSLSPGK

HU6DL.A54 LC

SEQ ID NO: 15

DVVMTQSPLSLPVTLGQPASISCKASQDVSTAVAWYQQKPGKAPKLFIYSASYR

YTGVPSRFSGSGSGTDFTLTISSLQPEDFATYYCQQHYSTPLTFGQGTRLEIKRTV

AAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC.

TABLE 4

The sequences of heavy chain variable region HCDR2 of HU6DL mutants

| Name | Sequence | No. |
|---|---|---|
| HU6DL.R54 | RIDPRDSETHYNQKFKD | SEQ ID NO: 26 |
| HU6DL.Y54 | RIDPYDSETHYNQKFKD | SEQ ID NO: 27 |
| HU6DL.Q54 | RIDPQDSETHYNQKFKD | SEQ ID NO: 28 |
| HU6DL.L54 | RIDPLDSETHYNQKFKD | SEQ ID NO: 29 |
| HU6DL.T54 | RIDPTDSETHYNQKFKD | SEQ ID NO: 30 |

TABLE 4-continued

The sequences of heavy chain variable region HCDR2 of HU6DL mutants

| Name | Sequence | No. |
|---|---|---|
| HU6DL.I54 | RIDPIDSETHYNQKFKD | SEQ ID NO: 39 |
| HU6DL.F54 | RIDPFDSETHYNQKFKD | SEQ ID NO: 40 |
| HU6DL.E54 | RIDPEDSETHYNQKFKD | SEQ ID NO: 41 |
| HU6DL.A54 | RIDPADSETHYNQKFKD | SEQ ID NO: 42 |

TABLE 5

| Sequence Nos. of HU6DL mutants | | | | | |
|---|---|---|---|---|---|
| Name | Heavy chain/ light chain No. | Heavy chain/ light chain variable region No. | Heavy chain/ light chain CDR1 No. | Heavy chain/ light chain CDR2 No. | Heavy chain/ light chain CDR3 No. |
| HU6DL.R54 | SEQ ID NO: 21 (heavy chain) | SEQ ID NO: 16 (heavy chain variable region) | SEQ ID NO: 4 | SEQ ID NO: 26 | SEQ ID NO: 6 |
| | SEQ ID NO: 15 (light chain) | SEQ ID NO: 11 (light chain variable region) | SEQ ID NO: 7 | SEQ ID NO: 8 | SEQ ID NO: 9 |
| HU6DL.Y54 | SEQ ID NO: 22 (heavy chain) | SEQ ID NO: 17 (heavy chain variable region) | SEQ ID NO: 4 | SEQ ID NO: 27 | SEQ ID NO: 6 |
| | SEQ ID NO: 15 (light chain) | SEQ ID NO: 11 (light chain variable region) | SEQ ID NO: 7 | SEQ ID NO: 8 | SEQ ID NO: 9 |
| HU6DL.Q54 | SEQ ID NO: 23 (heavy chain) | SEQ ID NO: 18 (heavy chain variable region) | SEQ ID NO: 4 | SEQ ID NO: 28 | SEQ ID NO: 6 |
| | SEQ ID NO: 15 (light chain) | SEQ ID NO: 11 (light chain variable region) | SEQ ID NO: 7 | SEQ ID NO: 8 | SEQ ID NO: 9 |
| HU6DL.L54 | SEQ ID NO: 24 (heavy chain) | SEQ ID NO: 19 (heavy chain variable region) | SEQ ID NO: 4 | SEQ ID NO: 29 | SEQ ID NO: 6 |
| | SEQ ID NO: 15 (light chain) | SEQ ID NO: 11 (light chain variable region) | SEQ ID NO: 7 | SEQ ID NO: 8 | SEQ ID NO: 9 |
| HU6DL.T54 | SEQ ID NO: 25 (heavy chain) | SEQ ID NO: 20 (heavy chain variable region) | SEQ ID NO: 4 | SEQ ID NO: 30 | SEQ ID NO: 6 |
| | SEQ ID NO: 15 (light chain) | SEQ ID NO: 11 (light chain variable region) | SEQ ID NO: 7 | SEQ ID NO: 8 | SEQ ID NO: 9 |
| HU6DL.I54 | SEQ ID NO: 35 (heavy chain) | SEQ ID NO: 31 (heavy chain variable region) | SEQ ID NO: 4 | SEQ ID NO: 39 | SEQ ID NO: 6 |
| | SEQ ID NO: 15 (light chain) | SEQ ID NO: 11 (light chain variable region) | SEQ ID NO: 7 | SEQ ID NO: 8 | SEQ ID NO: 9 |
| HU6DL.F54 | SEQ ID NO: 36 (heavy chain) | SEQ ID NO: 32 (heavy chain variable region) | SEQ ID NO: 4 | SEQ ID NO: 40 | SEQ ID NO: 6 |
| | SEQ ID NO: 15 (light chain) | SEQ ID NO: 11 (light chain variable region) | SEQ ID NO: 7 | SEQ ID NO: 8 | SEQ ID NO: 9 |
| HU6DL.E54 | SEQ ID NO: 37 (heavy chain) | SEQ ID NO: 33 (heavy chain variable region) | SEQ ID NO: 4 | SEQ ID NO: 41 | SEQ ID NO: 6 |
| | SEQ ID NO: 15 (light chain) | SEQ ID NO: 11 (light chain variable region) | SEQ ID NO: 7 | SEQ ID NO: 8 | SEQ ID NO: 9 |
| HU6DL.A54 | SEQ ID NO: 38 (heavy chain) | SEQ ID NO: 34 (heavy chain variable region) | SEQ ID NO: 4 | SEQ ID NO: 42 | SEQ ID NO: 6 |
| | SEQ ID NO: 15 (light chain) | SEQ ID NO: 11 (light chain variable region) | SEQ ID NO: 7 | SEQ ID NO: 8 | SEQ ID NO: 9 |

The cDNA fragments were synthesized according to the amino acid sequences of the above humanized antibody light chain and heavy chains. Protein expression services were provided by Beijing Sinobiological Co., Ltd. HEK293 cells were transiently transfected with HU6DL protein mutants for expression The antibodies were detected for their purity by using molecular exclusion chromatography, and their concentration and purity were as shown in Table 6 below.

TABLE 6

| Concentration and purity of HU6DL mutants | | |
|---|---|---|
| Name | Concentration (mg/mL) | Purity (%) |
| HU6DL.R54 | 1.99 | 95.8 |
| HU6DL.Y54 | 1.34 | 96.4 |
| HU6DL.Q54 | 1.73 | 93.1 |
| HU6DL.L54 | 1.36 | 94.9 |

TABLE 6-continued

| Concentration and purity of HU6DL mutants | | |
|---|---|---|
| Name | Concentration (mg/mL) | Purity (%) |
| HU6DL.T54 | 2.73 | 96.1 |
| HU6DL.I54 | 2.00 | 95.5 |
| HU6DL.F54 | 1.68 | 93.5 |
| HU6DL.E54 | 1.56 | 95.6 |
| HU6DL.A54 | 1.00 | 95.1 |

Example 6. Affinity Experiment of HU6DL Mutants to TROP-2 Antigen

1. Objective of the Experiment:

The difference in affinity level of different anti-TROP-2 mutants to TROP-2 antigen was evaluated by sandwich ELISA, i.e., "antigen-antibody-HRP-labeled secondary antibody".

2. Experimental Steps:

The his-tagged TROP-2 protein (SinoBiologics, Cat: 10428-H08H) was diluted to 1 μg/mL using DPBS pH 7.4, and added to a high-affinity 96-well plate (Corning, Cat: 3590) at 100 μL/well and incubated overnight at 4° C. On the next day, the TROP-2 antigen solution was discarded. PBS pH 7.4 comprising 0.05% Tween 20™ (PBST) solution was added at 200 μL/well for washing 3 times. 2% BSA (dissolved in PBST) was added at 200 μL/well for blocking at 37° C. for 1 h and the plate was washed 3 times with PBST. Serial dilutions of the candidate antibody (10-fold dilutions giving 8 concentration levels from 10 nM to $1\times10^{-6}$ nM) were added at 100 μL/well, with 0.5% BSA used as a negative control, and incubated at 37° C. for 1 h for blocking. The plate was washed 3 times with PBST. Goat anti-human IgG, Fc-HRP (Abcam, cat: ab97225) secondary antibody solution diluted at 1:10000 was added at 100 μL/well and incubated at 37° C. for 1 h for blocking. The plate was washed 3 times with PBST.

TMB (CST, Cat: 7004P6) substrate was added at 100 μL/well for reaction at room temperature for 3 min, until the color of the solution in the well with highest antibody concentration changed to dark blue. Stop solution (CST, Cat: 7002P6) was added at 50 μL/well to terminate the reaction. The absorbance (OD) was read at a wavelength of 450 nm.

3. Data Processing:

The $EC_{50}$ (the affinity of each HU6DL mutant to the antigen) was calculated by plotting, with the logarithmic concentration of the candidate antibody as the X-coordinate and the OD450 absorbance as the Y-coordinate, and fitting against log (agonist) vs. response-viable slope (four-parameter) equation in GRAPHPAD PRISM™ 8.0. The affinity ($EC_{50}$) of HU6DL mutants to human TROP-2 antigen was as shown in Table 7 below:

TABLE 7

| Affinity of HU6DL mutants to human TROP-2 antigen ($EC_{50}$) | | |
|---|---|---|
| Name | TOP $OD_{450}$ | Affinity $EC_{50}$ (nM) |
| HU6DL.R54 | 2.05 | 0.052 |
| HU6DL.Y54 | 1.93 | 0.051 |
| HU6DL.Q54 | 1.91 | 0.086 |
| HU6DL.L54 | 1.96 | 0.048 |

TABLE 7-continued

| Affinity of HU6DL mutants to human TROP-2 antigen ($EC_{50}$) | | |
|---|---|---|
| Name | TOP $OD_{450}$ | Affinity $EC_{50}$ (nM) |
| HU6DL.T54 | 1.90 | 0.052 |
| HU6DL.I54 | 1.96 | 0.063 |
| HU6DL.F54 | 1.93 | 0.067 |
| HU6DL.E54 | 1.96 | 0.064 |
| HU6DL.A54 | 2.07 | 0.062 |

4. Conclusion of the Experiment:

The above data show that each HU6DL mutant of the present disclosure has good affinity to human TROP-2 antigen.

Example 7: Affinity Experiment of HU6DL Mutants on Tumor Cells

1. Objective of the Experiment:

The difference in affinity levels of HU6DL mutants to tumor cell lines expressing TROP-2 antigen was evaluated by flow cytometry.

2. Experimental Reagents:

Gastric cancer cell NCI-N87 (purchased from Chinese Academy of Sciences Cell Bank, TCHul30);

non-small cell lung cancer cell HCC827 (purchased from Chinese Academy of Sciences Cell Bank, TCHul53);

bladder cancer cell SW780 (purchased from Chinese Academy of Sciences Cell Bank, TCHu219);

bladder cancer cell RT4 (purchased from Chinese Academy of Sciences Cell Bank, TCHu226).

3. Experimental Steps:

Tumor cells in a well-growing state were treated with Accutase (Sigma, cat: A6964) digestion solution. Single-cell suspension was prepared in 2% FBS (diluted in DBPS, pH 7.4) solution and the cell concentration was adjusted to $1\times10^{6}$ cells/mL. The suspension was aliquoted into a 96-well V-shaped bottom plate at 100 μL/well and centrifuged at 300 g×5 min at 4° C. The supernatant was discarded, and serial dilution of the candidate antibody solution (10-fold dilution giving 10 concentration levels from 1000 nM to $1\times10^{-6}$ nM) was added at 100 μL/well and incubated at 4° C. for 1 h.

The plate was centrifuged at 300 g×5 min at 4° C. and washed twice. Mouse-anti-human IgG Fc, PE-labeled secondary antibody (Biolegend, cat: 409304) solution diluted at a ratio of 5 μL/$10^{6}$ cells was added at 100 μL/well and incubated at 4° C. for 1 h. The plate was centrifuged at 300 g×5 min at 4° C. and washed twice. 70 μL of 2% FBS solution was added to resuspend the cells. The mean fluorescence intensity (MFI) of the PE channel was detected by a ZE5 flow cytometry (Bio-Rad, ZE5).

4. Data Processing:

The $EC_{50}$ (the affinity of each candidate antibody to the tumor cells) was calculated by plotting, with the logarithmic concentration of the mutant antibody as the X-coordinate and the MFI as the Y-coordinate and fitting against log (agonist) vs. response-viable slope (four-parameter) equation in GRAPHPAD PRISM™ 8.0, as shown in Table 8 below:

TABLE 8

Affinity of HU6DL mutants to NCI-N87, HCC827, SW780 and RT4 tumor cells ($EC_{50}$)

| Name | NCI-N87 TOP MFI | NCI-N87 $EC_{50}$ (nM) | HCC827 TOP MFI | HCC827 $EC_{50}$ (nM) | SW780 TOP MFI | SW780 $EC_{50}$ (nM) | RT4 TOP MFI | RT4 $EC_{50}$ (nM) |
|---|---|---|---|---|---|---|---|---|
| HU6DL.R54 | 2693 | 1.63 | 6088 | 1.36 | 6581 | 1.22 | 3231 | 1.21 |
| HU6DL.T54 | 1703 | 2.25 | 4563 | 1.46 | 4850 | 1.20 | 2254 | 1.31 |
| HU6DL.A54 | 1573 | 4.23 | 4143 | 2.48 | 4590 | 1.88 | 2221 | 2.81 |
| HU6DL.I54 | 1933 | 4.66 | 4219 | 2.25 | 4542 | 2.42 | 2458 | 6.11 |

5. Conclusion of the Experiment:

The above data show that each HU6DL mutant of the present disclosure has good affinity to NCI-N87, HCC827, SW780 and RT4 tumor cells.

Example 8: HU6DL Mutant-Mediated TROP2 Endocytosis Experiment

1. Objective of the Experiment:

The antibody endocytic activity of HU6DL mutants was evaluated by flow cytometry, on tumor cell lines expressing TROP-2 antigen.

2. Experimental Steps:

Gastric cancer cells NCI-N87 (purchased from Chinese Academy of Sciences Cell Bank, TCHul30) in a well-growing state were treated with Accutase (Sigma, cat: A6964) digestion solution. Single-cell suspension was prepared in 2% FBS (diluted in DBPS, pH 7.4) solution and the cell concentration was adjusted to $1\times10^7$ cells/mL. The suspension was aliquoted into a 96-well V-shaped bottom plate at 100 μL/well. The candidate antibody solution was added at a final concentration of 20 μg/mL, mixed well and incubated at 4° C. for 1 h.

The plate was centrifuged at 300 g×5 min at 4° C. Mouse-anti-human IgG Fc, PE-labeled secondary antibody (Biolegend, cat: 409304) solution diluted at a ratio of 5 μL/$10^6$ cells was added at 100 μL/well and incubated at 4° C. for 1 h.

The plate was centrifuged at 300 g×5 min at 4° C. and washed twice. The cell pellet was resuspended in 1 mL of pre-warmed complete medium and aliquoted into four groups, namely the 0 min group, the blank group, the 30 min group and the 120 min group, respectively. The 0 min group and the blank control were placed on ice. The rest were placed in an incubator at 37° C. for endocytosis for 30 min and 120 min, respectively. The group was taken out at the corresponding time point and pre-cooled on ice for 5 min. All treatment groups were centrifuged and the supernatant was discarded (4° C., 1500 rpm×5 min). The cells were washed once with Fluorescence-Activated Cell Sorting buffer and the supernatant was discarded. 250 μL of strip buffer was added to all treatment groups except the 0 min group, incubated at room temperature for 8 min and centrifuged (4° C., 1500 rpm×5 min), and the supernatant was discarded. The cells were washed twice with Fluorescence-Activated Cell Sorting buffer and the supernatant was discarded. 80 μL of 2% FBS were added to each group of sample to resuspend the cells. The fluorescence signal of the sample to be tested was detected by a ZE5 flow cytometry (Bio-Rad, ZE5).

3. Data Processing:

The endocytosis rate of each candidate antibody was calculated according to the following equation: antibody endocytosis percentage (%)=(MFI of treatment group−MFI of blank control group)/(MFI of 0 min group−MFI of blank control group)×100%. The endocytosis rate of HU6DL mutants was detected by the above method and was as shown in Table 9:

TABLE 9

The endocytosis rate of HU6DL mutants by NCI-N87 cells

| Name | Antibody endocytosis (%) 30 min | 120 min |
|---|---|---|
| HU6DL.R54 | 64 | 62 |
| HU6DL.Y54 | 71 | 71 |
| HU6DL.Q54 | 71 | 71 |
| HU6DL.L54 | 76 | 72 |
| HU6DL.T54 | 63 | 69 |
| HU6DL.I54 | 65 | 66 |
| HU6DL.F54 | 72 | 75 |
| HU6DL.E54 | 75 | 72 |
| HU6DL.A54 | 72 | 70 |

4. Conclusion of the Experiment:

The above data show that the HU6DL mutants of the present disclosure are well endocytosed in gastric cancer cells NCI-N87 mediated by the TROP-2 protein.

Example 9: Detection of Impurity Components of HU6DL Mutants

1. Objective of the experiment: The content and change in level of the impurity peaks of the mutated antibodies were detected and compared, by capillary electrophoresis based on the Maurice-nrCE-SDS method.

2. Experimental Steps 2.1. Sample Preparation:

(1) Buffer exchange and concentration of samples: Buffer exchange and concentration of samples were required when the protein concentration of the sample was less than 5 mg/ml, or when the salt concentration in the sample buffer was high, so as to ensure a protein concentration of about 5 mg/ml and a salt concentration in the sample of less than 50 mM.

(2) Non-reducing processing of CE samples: The sample was added to an EP tube at an amount of 50 μg protein taken for each sample. 1 μl of 10 kD internal standard (Protein Simple, 046-144) was added, 2.5 μl of 250 mM IAM (Sigma, I1149-5G) was added, and 1×sample buffer (Protein Simple, 046-567) was added to a final volume of 50 μl.

(3) The sample was mixed well by shaking, heated and incubated at 70° C. for 10 min, and then taken out. The sample was incubated on ice for 5 min until cool and then centrifuged at 12,000 rpm for 5 min. After centrifugation, 35 μl of supernatant was transferred to a 96-well sample plate that matched the instrument, and then centrifuged at 1,000 rpm for 5 min. The 96-well sample plate was placed in Maurice (Protein Simple) for sample loading and analysis.

2.2. Detection on an Instrument

The instrument was turned on and the software was opened. The instrument self-checking was performed according to the instrument operation steps. The capillary cartridge was installed and the prepared corresponding reagents were put into the corresponding position in the instrument. The corresponding parameters were set and non-reducing CE analysis was performed according to the instrument operation steps. The sample sequence was set by editing the corresponding sequence according to the sample name, and the number of samples for each sequence would not exceed 48. After completion of sequence editing, detection of the sequence was started by clicking Start.

The content of the main peak and impurity peak of the sample was calculated using the following equation.

$$\text{Non-reducing purity } (\%) = \frac{CA_{main\ peak}}{CA_{total}} \times 100\%$$

Note:

In the equation, the non-reducing purity is the percentage of corrected main peak area;

$CA_{main\ peak}$ is the corrected main peak area;

$CA_{total}$ is the sum of the corrected main peak and impurity peak areas.

3. Results of the Experiment:

TABLE 10

Detection of impurity components

| Sample | Main peak content (%) | Impurity peak content (%) |
|---|---|---|
| HU6DL.T54 | 93.62 | N/A |
| HU6DL | 84.78 | 4.72 |

The above data show that the main peak content of the sample HU6DL.T54 reached 93.62%, and no impurities were detected. The experimental results show that the $N^{54}D^{55}S^{56}$ motif in HCDR2 of HU6DL is susceptible to glycosylation, and site-directed mutation of N54 can effectively reduce glycosylated impurities and achieve better purity.

Example 10: Competitive Binding of Humanized Antibodies to Antigen

1. Objective of the experiment: The binding mode and binding site of different antibodies to antigen was studied by competitive binding experiments.

2. Experimental Steps

The coating antibodies hRS7 and HU6DL mutants were diluted with pH 7.4 PBS to a concentration of 1 μg/ml, added to a 96-well high-affinity ELISA plate at 100 μl/well and incubated in a refrigerator at 4° C. overnight (16-20 hours). After washing the plate 4 times with PBST (pH 7.4 PBS comprising 0.05% Tween-20™), 2% bovine serum albumin (BSA) blocking solution diluted with PBST was added at 200 μl/well and incubated at room temperature for 1 hour for blocking. After completion of the blocking, the blocking solution was discarded, and the plate was washed 4 times with PBST buffer.

The competing antibodies hRS7 and HU6DL were diluted to 100 μg/ml with PBST comprising 0.5% BSA and added to the ELISA plate at 50 μl/well. TROP-2 His protein (Acro biosystems, cat #TR2-H5223) was diluted with PBST comprising 0.5% BSA at concentrations corresponding to affinity $2\times EC_{80}$ or $2\times EC_{90}$ of TROP-2 His protein to the coating antibody, respectively, and added to the ELISA plate at 50 μl/well. The ELISA plate was incubated at room temperature for 1 hour. After completion of the incubation, the plate was washed 4 times with PBST. Anti-His HRP labeled secondary antibody (Sino Biological, cat #105327-MM02T-H) diluted with PBST comprising 0.5% BSA at 1:5000 was added at 100 μl/well and incubated at room temperature for 1 h. The plate was washed 4 times with PBST, then TMB chromogenic substrate (Cell Signaling Technology, cat #7004S) was added at 100 μl/well and incubated at room temperature in the dark for 1 minute. The stop solution (Cell Signaling Technology, cat #7002S) was added at 50 μl/well to terminate the reaction.

3. Data Processing

The absorbance at 450 nm was read with a microplate reader (Thermo, model VARIOSKAN LUX™) and the data were analyzed, as shown in Table 11 below.

TABLE 11

Competitive binding of humanized antibodies and hRS7 to antigen

| Humanized antibody | Inhibition rate |
|---|---|
| hRS7 | 94.67% |
| HU6DL.T54 | 23.30% |

4. Results of the Experiment

The mutationally modified humanized antibody of the present invention has a very low inhibition rate on the binding of hRS7 antibody to TROP2 protein, suggesting that the mutationally modified humanized antibody of the present invention and hRS7 antibody do not competitively bind the same epitope.

What is claimed is:

1. An anti-TROP-2 antibody, an antigen-binding fragment thereof or a mutant thereof, which comprises a heavy chain variable region and a light chain variable region, wherein, the heavy chain variable region comprises HCDR1 as shown in SEQ ID NO: 4, HCDR2 as shown in SEQ ID NO: 43, and HCDR3 as shown in SEQ ID NO: 6, and the light chain variable region comprises LCDR1 as shown in SEQ ID NO: 7, LCDR2 as shown in SEQ ID NO: 8, and LCDR3 as shown in SEQ ID NO: 9.

2. The anti-TROP-2 antibody, antigen-binding fragment thereof or mutant thereof according to claim 1, wherein the antibody is a murine antibody, a chimeric antibody, or a humanized antibody.

3. The anti-TROP-2 antibody, antigen-binding fragment thereof or mutant thereof according to claim 1, wherein:

the anti-TROP-2 antibody, antigen-binding fragment thereof or mutant thereof further comprises a constant region derived from human IgG1, IgG2, IgG3 or IgG4 or a mutant thereof.

4. The anti-TROP-2 antibody, antigen-binding fragment thereof or mutant thereof according to claim 3, wherein the anti-TROP-2 antibody, antigen-binding fragment thereof or mutant thereof further comprises a light chain constant region derived from human κ chain, λ chain or a mutant thereof.

5. The anti-TROP-2 antibody, antigen-binding fragment thereof or mutant thereof according to claim 1, wherein the anti-TROP-2 antibody, antigen-binding fragment thereof or mutant thereof comprises a heavy chain variable region selected from the group consisting of SEQ ID NO: 20, SEQ ID NO: 16, SEQ ID NO: 17, SEQ ID NO: 18, SEQ ID NO: 19, SEQ ID NO: 31, SEQ ID NO: 32, SEQ ID NO: 33, SEQ ID NO: 34, or a heavy chain variable region having at least 70%, 75%, 80%, 85%, 90%, 95% or 99% identity with the same.

6. The anti-TROP-2 antibody, antigen-binding fragment thereof or mutant thereof according to claim 1, wherein the anti-TROP-2 antibody, antigen-binding fragment thereof or mutant thereof comprises the light chain variable region of SEQ ID NO: 11, or a light chain variable region having at least 70%, 75%, 80%, 85%, 90%, 95% or 99% identity with the same.

7. The anti-TROP-2 antibody, antigen-binding fragment thereof or mutant thereof according to claim 5, wherein the anti-TROP-2 antibody or mutant thereof comprises a heavy chain selected from the group consisting of SEQ ID NO: 25, SEQ ID NO: 21, SEQ ID NO: 22, SEQ ID NO: 23, SEQ ID NO: 24, SEQ ID NO: 35, SEQ ID NO: 36, SEQ ID NO: 37, SEQ ID NO: 38, or a heavy chain having at least 80%, 85%, 90%, 95% or 99% identity with the same.

8. The anti-TROP-2 antibody, antigen-binding fragment thereof or mutant thereof according to claim 5, wherein the anti-TROP-2 antibody or mutant thereof comprises the light chain of SEQ ID NO: 15, or a light chain having at least 80%, 85%, 90%, 95% or 99% identity with the same.

9. The anti-TROP-2 antibody, antigen-binding fragment thereof or mutant thereof according to claim 1, wherein:

the anti-TROP-2 antibody, antigen-binding fragment thereof or mutant thereof comprises the heavy chain variable region as shown in SEQ ID NO: 20, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 16, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 17, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 18, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 19, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 31, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 32, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 33, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same; or, the anti-TROP-2 antibody, antigen-binding fragment thereof or mutant thereof comprises the heavy chain variable region as shown in SEQ ID NO: 34, or a heavy chain variable region having at least 70%, 75%, 80%, 85%, 90%, 95% or 99% identity with the same, and the light chain variable region as shown in SEQ ID NO: 11, or a light chain variable region having at least 70%, 75%, 80%, 85%, 90%, 95% or 99% identity with the same.

10. The anti-TROP-2 antibody, antigen-binding fragment thereof or mutant thereof according to claim 1, wherein:

the anti-TROP-2 antibody or mutant thereof comprises the heavy chain as shown in SEQ ID NO: 25, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 21, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 22, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 23, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 24, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 35, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 36, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 37, or a heavy chain having at least 80%, 85%, 90%, 95% or 99% identity with the same, and the light chain as shown in SEQ ID NO: 15, or a light chain having at least 80%, 85%, 90%, 95% or 99% identity with the same; or, the anti-TROP-2 antibody or mutant thereof comprises the heavy chain as shown in SEQ ID NO: 38, or a heavy chain having at least 80%, 85%, 90%, 95% or 99% identity with the same, and the light chain as shown in SEQ ID NO: 15, or a light chain having at least 80%, 85%, 90%, 95% or 99% identity with the same.

11. A polynucleotide encoding the anti-TROP-2 antibody, antigen-binding fragment thereof or mutant thereof according to claim 1.

12. An expression vector comprising the polynucleotide according to claim 11.

13. A host cell transformed with the expression vector according to claim 12, wherein the host cell is selected from the group consisting of bacterium, yeast and mammalian cell.

14. A method of producing the anti-TROP-2 antibody, antigen-binding fragment thereof or mutant thereof according to claim 1, the method comprising:

culturing the host cell according to claim 13;

isolating the antibody from the culture, and purifying the antibody.

15. A pharmaceutical composition comprising the anti-TROP-2 antibody, antigen-binding fragment thereof or mutant thereof according to claim 1, as well as a pharmaceutically acceptable excipient, diluent or carrier.

16. A detection or diagnostic reagent comprising the anti-TROP-2 antibody, antigen-binding fragment thereof or mutant thereof according to claim 1.

17. A method for treating cancer expressing TROP-2 in a patient in need thereof, the method comprising administering to the patient the anti-TROP-2 antibody, antigen-binding fragment thereof or mutant thereof according to claim 1, or the pharmaceutical composition according to claim 15, wherein the cancer is selected from the group consisting of breast cancer, non-small cell lung cancer, ovarian cancer, prostate cancer, pancreatic cancer, kidney cancer, lung cancer, liver cancer, gastric cancer, colon cancer, bladder cancer, esophageal cancer, cervical cancer, gallbladder cancer, glioblastoma and melanoma.

18. A method for detecting, diagnosing or prognosing a TROP-2-mediated disease or condition in a patient in need thereof, the method comprising administering to the patient the anti-TROP-2 antibody, antigen-binding fragment thereof or mutant thereof according to claim 1, or the detection or diagnostic reagent according to claim 16.

19. The anti-TROP-2 antibody, antigen-binding fragment thereof or mutant thereof according to claim 1, wherein:

the heavy chain variable region comprises HCDR1 as shown in SEQ ID NO: 4, HCDR2 as shown in SEQ ID NO: 30, and HCDR3 as shown in SEQ ID NO: 6, the light chain variable region comprises LCDR1 as shown in SEQ ID NO: 7, LCDR2 as shown in SEQ ID NO: 8, and LCDR3 as shown in SEQ ID NO: 9; or, the heavy chain variable region comprises HCDR1 as shown in SEQ ID NO: 4, HCDR2 as shown in SEQ ID NO: 26, and HCDR3 as shown in SEQ ID NO: 6, the light chain variable region comprises LCDR1 as shown in SEQ ID NO: 7, LCDR2 as shown in SEQ ID NO: 8, and LCDR3 as shown in SEQ ID NO: 9; or, the heavy chain variable region comprises HCDR1 as shown in SEQ ID NO: 4, HCDR2 as shown in SEQ ID NO: 27, and HCDR3 as shown in SEQ ID NO: 6, the light chain variable region comprises LCDR1 as shown in SEQ ID NO: 7, LCDR2 as shown in SEQ ID NO: 8, and LCDR3 as shown in SEQ ID NO: 9; or, the heavy chain variable region comprises HCDR1 as shown in SEQ ID NO: 4, HCDR2 as shown in SEQ ID NO: 28, and HCDR3 as shown in SEQ ID NO: 6, the light chain variable region comprises LCDR1 as shown in SEQ ID NO: 7, LCDR2 as shown in SEQ ID NO: 8, and LCDR3 as shown in SEQ ID NO: 9; or, the heavy chain variable region comprises HCDR1 as shown in SEQ ID NO: 4, HCDR2 as shown in SEQ ID NO: 29, and HCDR3 as shown in SEQ ID NO: 6, the light chain variable region comprises LCDR1 as shown in SEQ ID NO: 7, LCDR2 as shown in SEQ ID NO: 8, and LCDR3 as shown in SEQ ID NO: 9; or, the heavy chain variable region comprises HCDR1 as shown in SEQ ID NO: 4, HCDR2 as shown in SEQ ID NO: 39, and HCDR3 as shown in SEQ ID NO: 6, the light chain variable region comprises LCDR1 as shown in SEQ ID NO: 7, LCDR2 as shown in SEQ ID NO: 8, and LCDR3 as shown in SEQ ID NO: 9; or, the heavy chain variable region comprises HCDR1 as shown in SEQ ID NO: 4, HCDR2 as shown in SEQ ID NO: 40, and HCDR3 as shown in SEQ ID NO: 6, the light chain variable region comprises LCDR1 as shown in SEQ ID NO: 7, LCDR2 as shown in SEQ ID NO: 8, and LCDR3 as shown in SEQ ID NO: 9; or, the heavy chain variable region comprises HCDR1 as shown in SEQ ID NO: 4, HCDR2 as shown in SEQ ID NO: 41, and HCDR3 as shown in SEQ ID NO: 6, the light chain variable region comprises LCDR1 as shown in SEQ ID NO: 7, LCDR2 as shown in SEQ ID NO: 8, and LCDR3 as shown in SEQ ID NO: 9; or, the heavy chain variable region comprises HCDR1 as shown in SEQ ID NO: 4, HCDR2 as shown in SEQ ID NO: 42, and HCDR3 as shown in SEQ ID NO: 6, the light chain variable region comprises LCDR1 as shown in SEQ ID NO: 7, LCDR2 as shown in SEQ ID NO: 8, and LCDR3 as shown in SEQ ID NO: 9.

20. The anti-TROP-2 antibody, antigen-binding fragment thereof or mutant thereof according to claim 3, wherein:

the anti-TROP-2 antibody, antigen-binding fragment thereof or mutant thereof further comprises a heavy chain constant region derived from a human IgG1, IgG2 or IgG4 mutant; or, the anti-TROP-2 antibody, antigen-binding fragment thereof or mutant thereof further comprises an IgG1 heavy chain constant region introduced with 239D and 241L mutations; or, the anti-TROP-2 antibody, antigen-binding fragment thereof or mutant thereof further comprises the heavy chain constant region of SEQ ID NO: 12.

21. The anti-TROP-2 antibody, antigen-binding fragment thereof or mutant thereof according to claim 4, wherein the anti-TROP-2 antibody, antigen-binding fragment thereof or mutant thereof further comprises the light chain constant region of SEQ ID NO: 13.

22. The host cell according to claim 13, wherein the host cell is selected from the group consisting of *Escherichia coli, Pichia pastoris*, CHO cell or HEK293 cell.

23. The method of producing the anti-TROP-2 antibody, antigen-binding fragment thereof or mutant thereof according to claim 14, wherein:

culturing the host cell according to claim 13 comprises culturing HEK293 cells; or, isolating the antibody from the culture comprises isolating the antibody from the cell culture fluid; or, purifying the antibody comprises purifying the antibody by chromatographic methods.

* * * * *